(12) United States Patent
Morck et al.

(10) Patent No.: US 6,667,040 B2
(45) Date of Patent: Dec. 23, 2003

(54) BOVINE FOOTROT TREATMENT AND PREVENTION

(75) Inventors: Douglas W. Morck, Airdrie (CA); Merle E. Olson, Calgary (CA)

(73) Assignee: University Technologies International, Inc., Alberta (CA)

( * ) Notice: Subject to any disclaimer, the term of this patent is extended or adjusted under 35 U.S.C. 154(b) by 0 days.

(21) Appl. No.: 09/834,904

(22) Filed: Apr. 16, 2001

(65) Prior Publication Data

US 2001/0028885 A1 Oct. 11, 2001

Related U.S. Application Data

(62) Division of application No. 09/148,778, filed on Sep. 4, 1998, now Pat. No. 6,241,992.
(60) Provisional application No. 60/058,167, filed on Sep. 8, 1997, and provisional application No. 60/085,540, filed on May 15, 1998.

(51) Int. Cl.$^7$ ..................... A61K 39/116; A61K 39/00; A61K 39/02; C12Q 1/00; G01N 33/554

(52) U.S. Cl. ................. 424/203.1; 424/184.1; 424/234.1; 424/236.1; 435/4; 435/7.32

(58) Field of Search .................... 424/203.1, 184.1, 424/234.1, 236.1; 435/4, 7.32, 243, 252.1, 69.3, 71.2, 71.3; 514/2, 12

(56) References Cited

U.S. PATENT DOCUMENTS

| | | |
|---|---|---|
| 5,288,617 A | 2/1994 | Mattick et al. |
| 5,536,497 A | 7/1996 | Evans et al. |
| 5,759,544 A | 6/1998 | Harada |
| 5,780,064 A | 7/1998 | Meisters et al. |
| 5,922,563 A | 7/1999 | Alderete |
| 6,162,429 A | 12/2000 | Wallis et al. |

FOREIGN PATENT DOCUMENTS

| | | |
|---|---|---|
| WO | WO92/03553 | 3/1992 |
| WO | WO99/12564 | 3/1999 |

OTHER PUBLICATIONS

Abraham, E.P., et al., "An Enzyme from Bacteria Able to Destroy Penicillin" [letter], *Nature*, 146:837 (1940).
Bennet, H.S., et al., "Science and Art of Preparing Tissues Embedded in Plastic for Light Microscopy, with Special Reference to Glycol Methacrylate, Glass Knives and Simple Stains", *Stain Technol*, 51: 71–97 (1976).
Berg, J.N., et al., "Fusobacterium necrophorum and *Bacteroides melaninogenicus* as Etiologic Agents of Footrot in Cattle", *Am J Vet Res*, 36(8):1115–1122 (1975).

Berg, J.N., "Bacterial Etiology of Diseases in the Footrot Complex: Recent Research and Nomenclature Changes", *Proceed and Abstr Eighth Internatl Symp on Disorders of the Ruminant Digit and Internatl Conf on Bovine Lameness*, Banff, Alberta, Canada, Univ. Saskatchewan Printing Services, p 51 (1994).
Bergsten, C., "Infectious Diseases of the Digits", *Lameness in Cattle*, 3rd Ed, Greenough, P.R. ed, W.B. Saunders Co., pp 89–100 (1997).
Blood, D.C., et al., *Veterinary Medicine: A Textbook of the Diseases of Cattle, Sheep, Pigs, Goats and Horses*, 6th Ed, London: Bailliere Tindall, pp 662–665 (1983).
Bradford, M.M., "A Rapid and Sensitive Method for the Quantitation of Microgram Quantities of Protein Utilizing the Principle of Protein–Dye Binding", *Annal Biochem*, 72:248–254 (1976).
Bush, K., "β–Lactamase Inhibitors from Laboratory to Clinic", *Clin Microbio Rev*, 1(1):109–123 (1988).
Chin, A., et al., "Anti–Inflammatory Benefits of Tilmicosin in the *Pasteurella haemolytica*–Infected Lung", (in press) (1998).
Egerton, J.R., "Footrot of Cattle, Goats, and Deer", *Footrot and Foot Abscess of Ruminants*, Egerton, J.R., et al. eds, CRC Press, pp 47–56 (1989).
Engelkrik, P.G., et al., "Principles and Practice of Clinical Anaerobic Bacteriology", Belmont: Star Publishing Co., pp 147–180 (1992).
Gillespie, J.H., et al., *Hagen and Bruner's Infections Diseases of Domestic Animals*, 7th Ed, Ithaca: Cornell University Press, p 158 (1981).
Gupta, R.B., et al., "A study of the Etiology of Footrot in Cattle", *Cornell Vet*, 54:66–77 (1994).
Heyermann, H., et al., "The Heterogeneity of Bovine $IgG_2$– V. Differences in the Primary Structure of Bovine $IgG_2$ Allotypes", *Mol Immun*, 29:1147–1152 (1992).
Kacsovics, I., et al., "The Heterogeneity of Bovine $IgG_2$– VIII. The Complete cDNA Sequence of Bovine $IgG_2$ (A2) and an IgG", *Mol Immun*, 33:189–195 (1996).
Kruse, G.O.W., et al., "Therapeutic Use of Terramycin Against Footrot in Cattle", *Proceedings* (vol. II), 15th World Buiatrios Congres, pp 1111–1116 (1988).
Kuby, *J Immun*, 2nd Ed, New York: W. H. Freeman and Co., pp 124–127 (1994).

(List continued on next page.)

*Primary Examiner*—Lynette R. F. Smith
*Assistant Examiner*—Vanessa L Ford
(74) *Attorney, Agent, or Firm*—Burns, Doane, Swecker & Mathis LLP

(57) ABSTRACT

This invention provides compositions and methods for treating or preventing footrot, in particular bovine footrot, by administering Porphyromonas and/or Prevotella and/or subunits and/or toxins thereof or neutralizing agents such as antibodies thereto. A model useful for evaluating the effectiveness of footrot treatments or preventatives is also provided.

7 Claims, 11 Drawing Sheets

OTHER PUBLICATIONS

Laemmli, U.K., "Cleavage of Structural Protein During the Assembly of the Head Bacteriophage T4", *Nature*, 227:680–685 (1970).

Lee, C.W., et al., "Evidence of Bovine Immunoglobulin $G_1$ ($IgG_1$) Protease Activity in Partially Purified Culture Supernate of *Pasteurella haemolytica* A1", *Can J Vet Res*, 60:127–132 (1996).

Loomes, et al., "The Cleavage of Immunoglobulin G in vitro and in vivo by a Proteinase Secreted by the Urinary Tract Pathogen *Proteus mirabilis*", *J Med Micro*, 39:225–232 (1993).

McGuire, T.C., et al., "Functional Properties of Bovine $IgG_1$ and $IgG_2$: Interaction with Complement, Macrophages, Neutrophils and Skin", *Immun*, 38:249–256 (1979).

Moellering, Robert C., Jr., "β–Lactamase Inhibition: Therapeutic Implications in Infectious Diseases—An Overview", *Rev of Infect Dis*, 13(Suppl 9):S723–726 (1991).

Morck, D.W., et al., "Experimental Evaluation of a Commercial Footrot Vaccine Against Native Canadian Strains of Dichelobacter Nodosus", *Can J Vet Res*, 58:122–126 (1994).

Morck, D.W., et al., "Comparison of ceftiofur sodium and oxytetracycline for treatment of acute interdigital phlegmon (foot rot) in feedlot cattle", *J Am Vet Med Assoc*, 212(2):254–257 (1988).

Mossman, et al, "Antibody–Dependent Cell–Mediated Cytotoxicity in Cattle: Transfer of IgG Subclasses in Relation to the Protection of the Newborn Calf", in Butler, et al., eds., *The Ruminant Immune System*, New York: Plenum Press, pp 279–291(1981).

Prokesova, et al., "Cleavage of Human Immunoglobulins by a Serine Protease from *Staphylococcus aureus*", *Immun Let*, 31:259–265 (1992).

Radostits, O.M., et al., "Bovine Interdigital Necrobacillosis (Foul in the Foot, Footrot)", *Vet Med: A Textbook of the Diseases of Cattle, Sheep, Pigs, Goats and Horses*, 8th Ed, Bailliere Tindall, pp 867–870 (1994).

Rolinson, G.N., "Evolution of β–Lactamase Inhibitors", *Rev of Infect Dis*, 13(Suppl 9):S727–732 (1991).

Sawyer, D.W., et al., "Polymorphonuclear Neutrophils: An Effective Antimicrobial Force", *Rev Infect Dis*, 11:S1532–S1544 (1989).

Schleif, Robert F., et al., *Practical Methods in Molec Biol*, Springer–Verlag, New York, Inc., pp 62–64 (1981).

Simpson, et al., "Purification, Characterization and Comparison of the Immunoglobulin A1 Proteases of *Neisseria gonorrhoeae*", *J Bact*, 170:1866–1873 (1988).

Taylor, C.E., "Cytokines as Adjuvants for Vaccines: Antigen–Specific Responses Differ from Polyclonal Responses", *Infect Immun*, 63:3241–3244 (1995).

Towbin, H., "Electrophoretic Transfer of Proteins from Polyacrylamide Gels to Nitrocellulose Sheets: Procedure and Some Applications", *Proc Natl Acad Sci*, 76:4350–4354 (1979).

Volar® *Fusobacterium necrophorum* Bacterin, Bayer, *Vet Pharm and Biologicals*, 10th Ed, pp 1024–1025 (1997).

Wassif et al., "Molecular Analysis of a Metalloprotease from *Proteus mirabilis*", *J Bact*, 177:5790–5798 (1995).

Sparrow, D.G., et al., Expression of Tumor Necrosis Factor α and Granulocyte–Macrophage Colony–Stimulating Factor by Bovine Endothelial Cells in Vitro, *Clin. Inf. Diseases*, 25(Supp 2):S178–179 (1997).

Takahashi et al., J. Dairy Science 75:1810–1820 (1992).

Vet. Pharmaceuticals and Biologicals pp. 1024–1025 (1997).

Amano et al., Infection and Immunity 62/8:3372–3380 (1994).

Hamada et al., Infection and Immunity 64:4788–4794 (1996).

Olson et al., Can J. Vet. Res. 62:33–37 (1998).

Lobb et al., Can J. Vet. Res. 63:113–118 (1999).

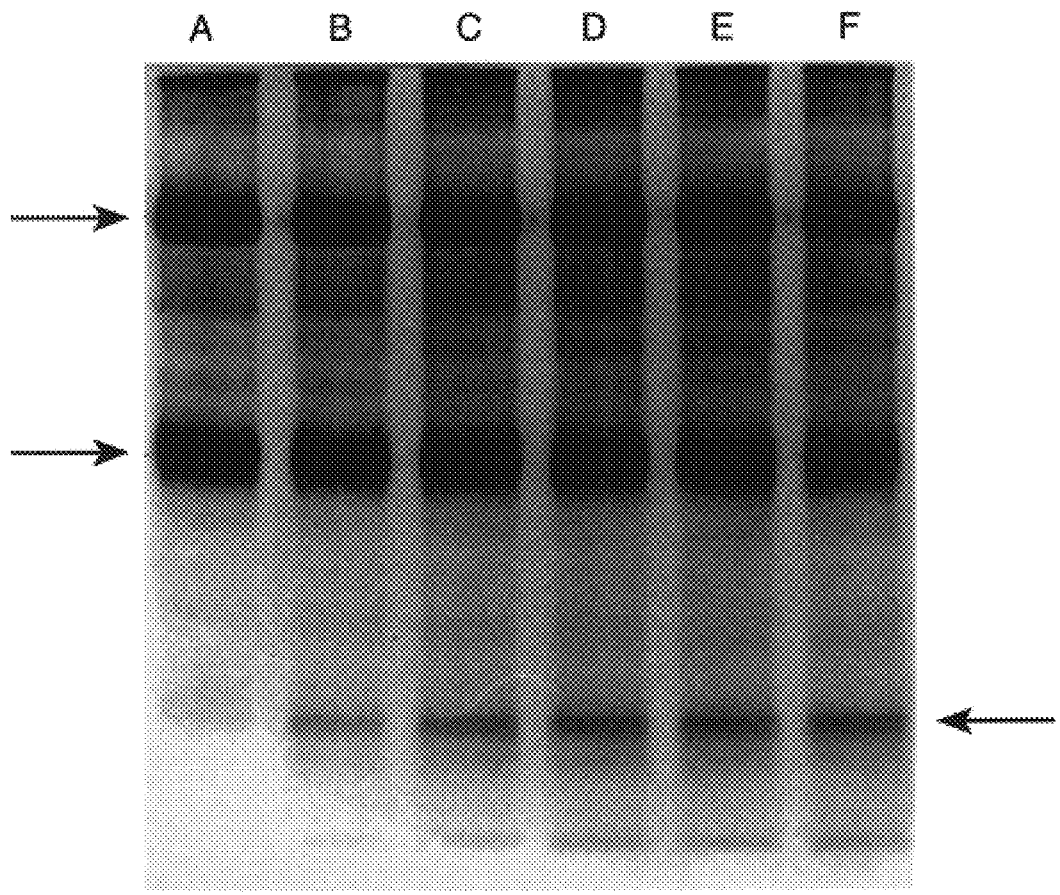
*FIG._1A*

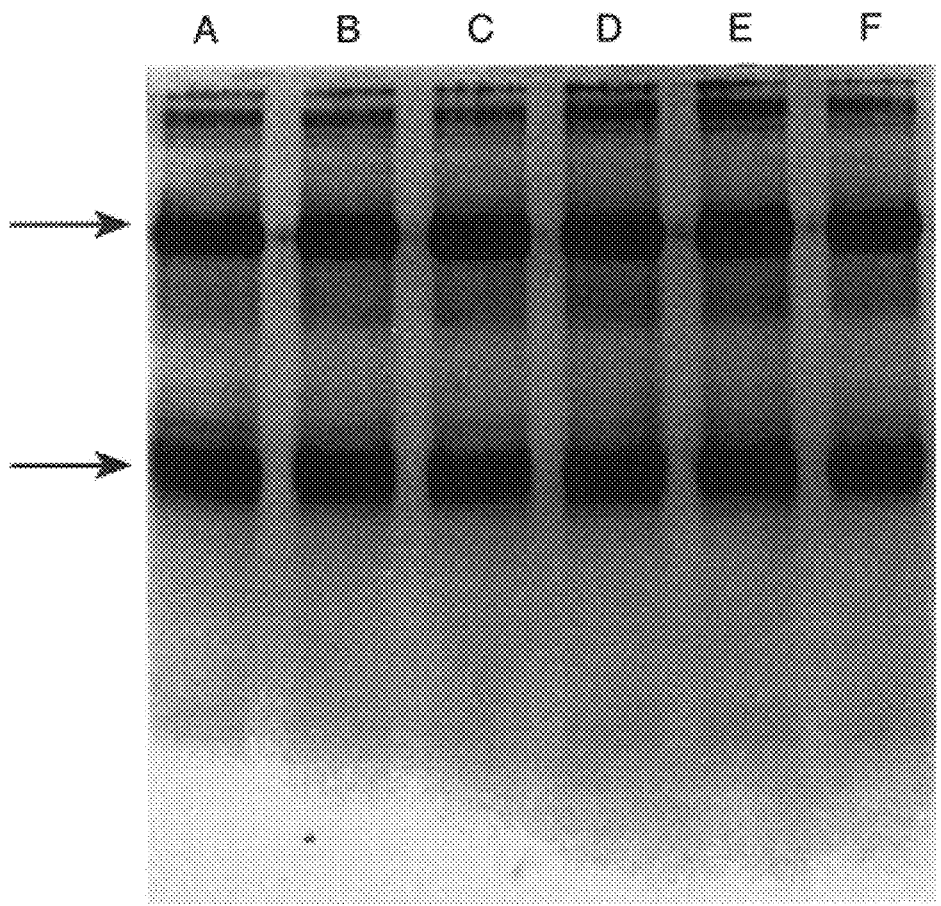
FIG._1B

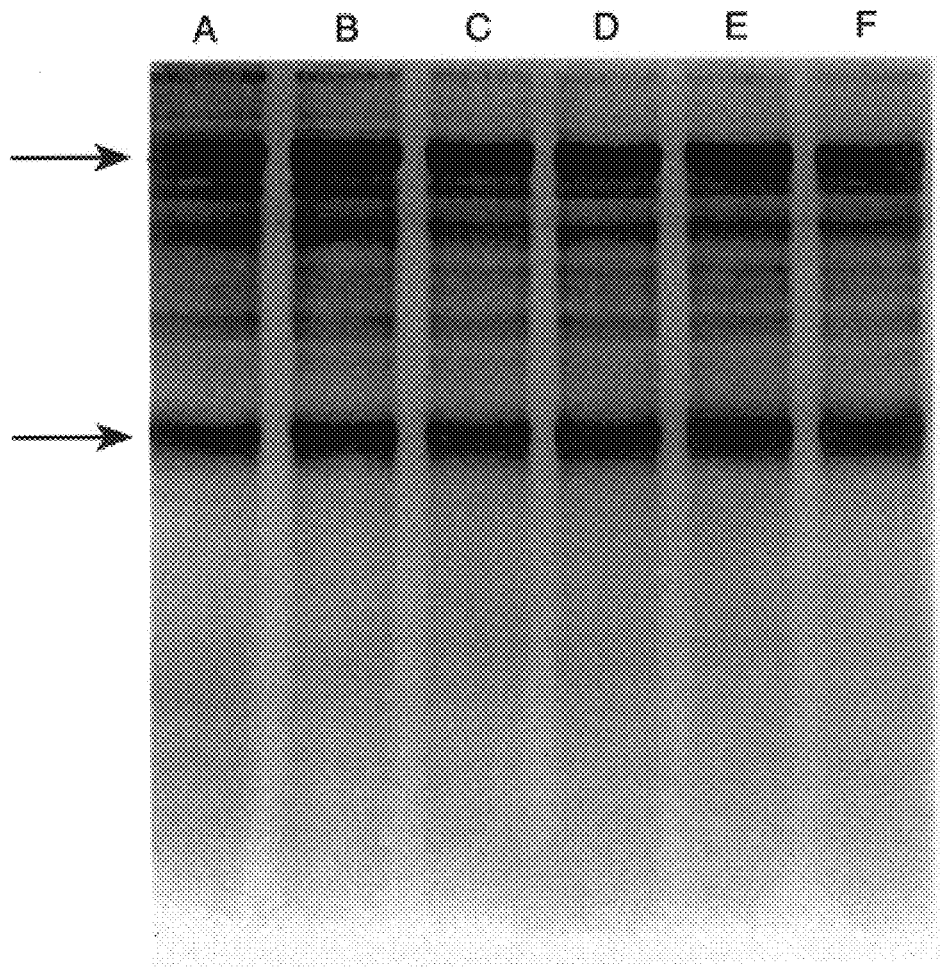
FIG._1C

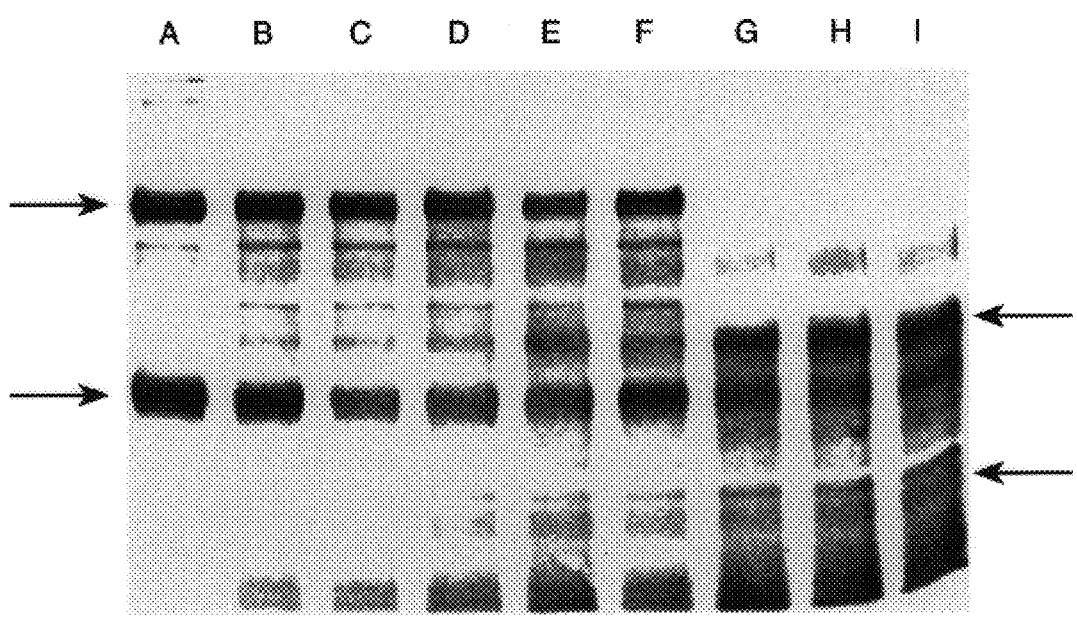
FIG._1D

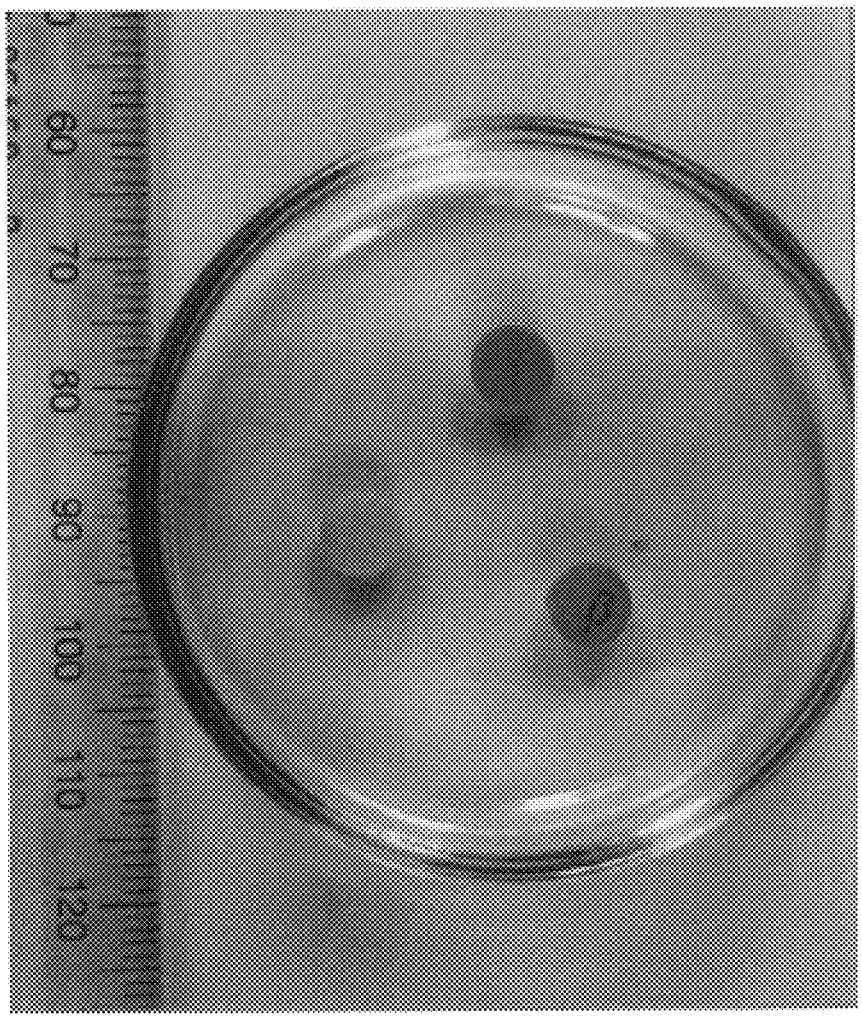
FIG._2

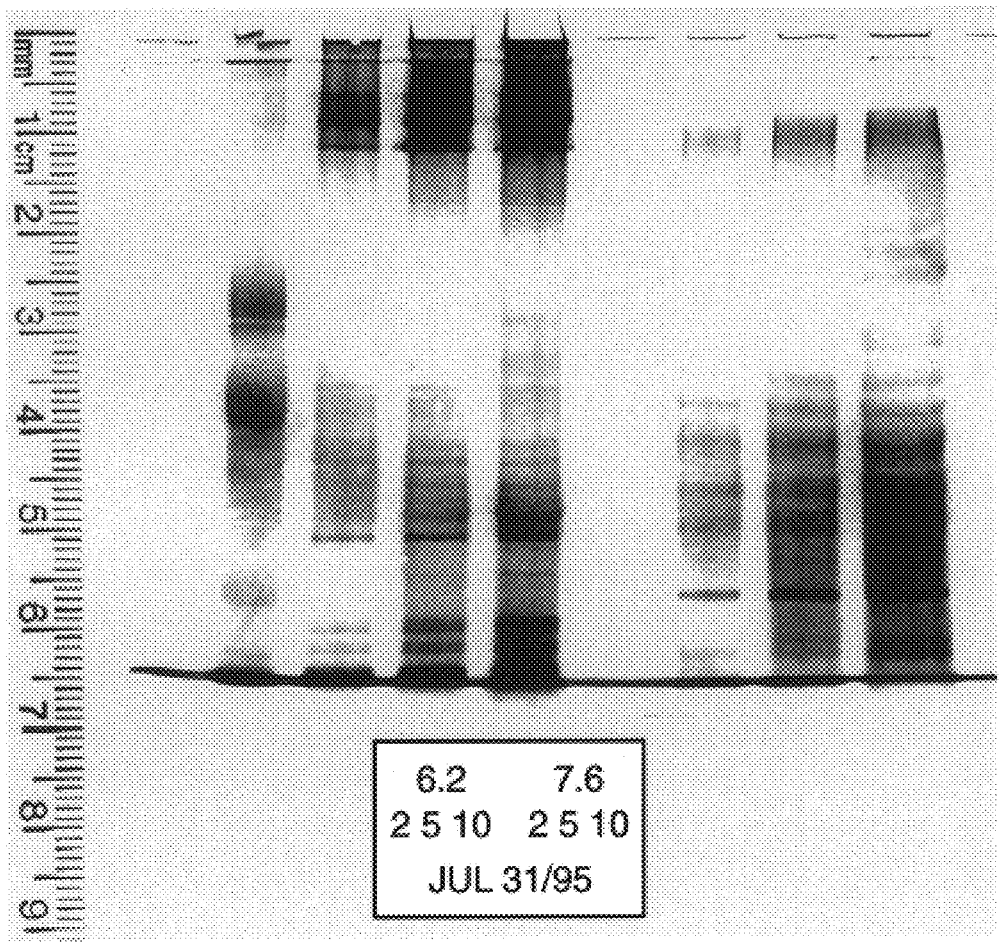
FIG._3

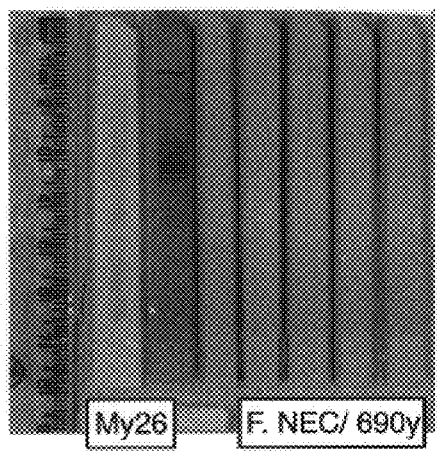
FIG._4A
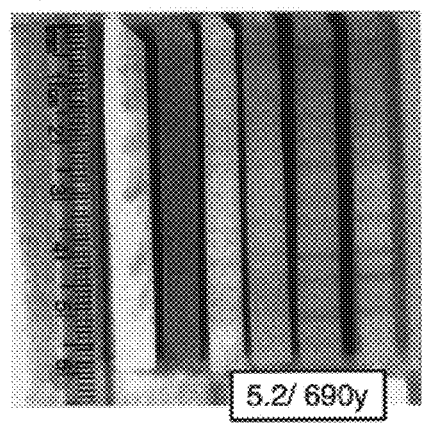
FIG._4B
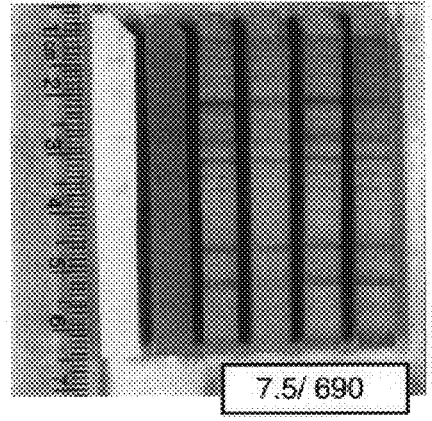
FIG._4C
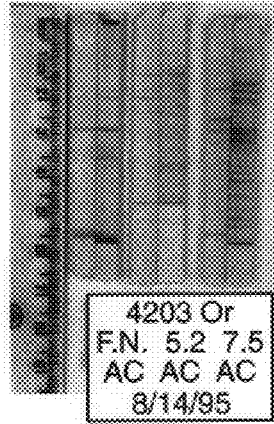
FIG._5A
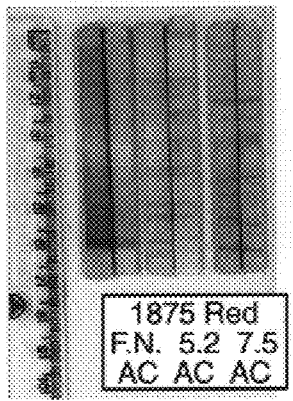
FIG._5B
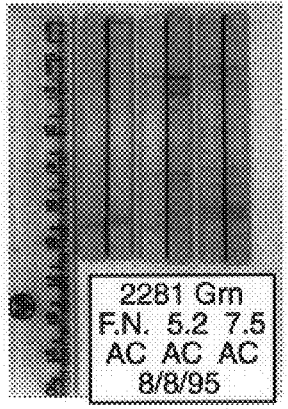
FIG._5C
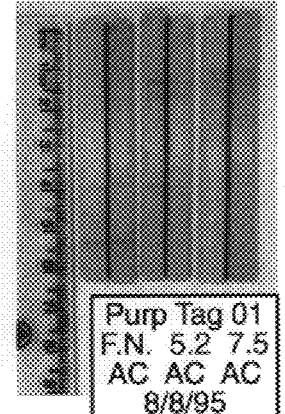
FIG._5D

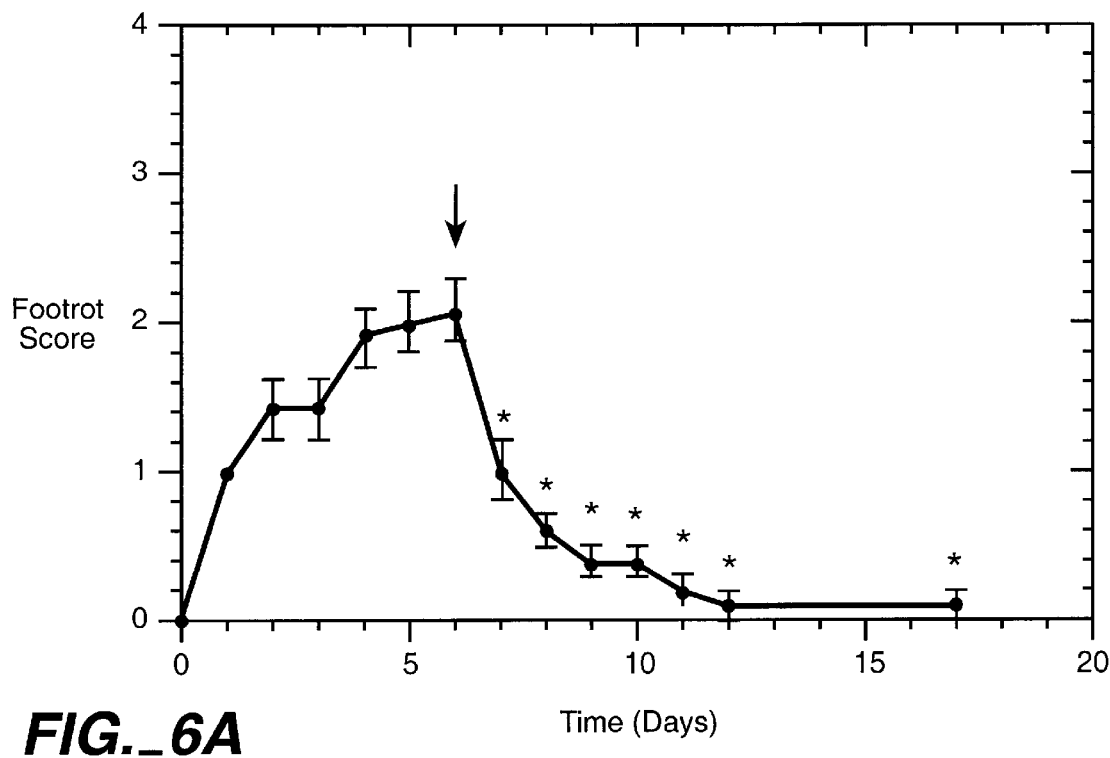
FIG._6A
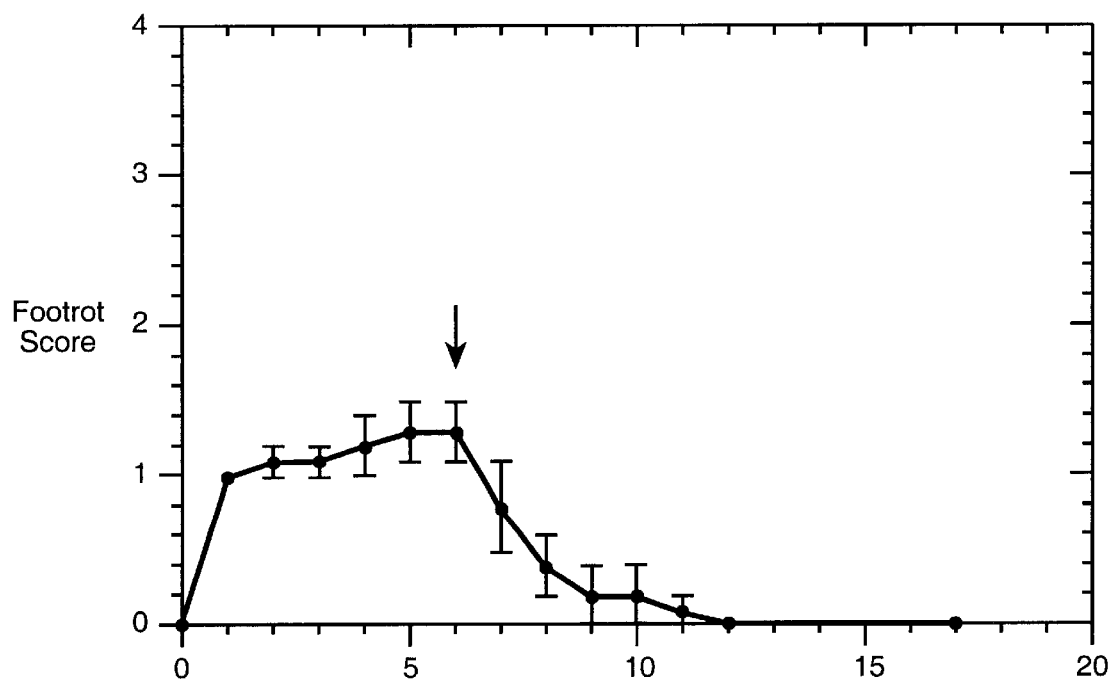
FIG._6B

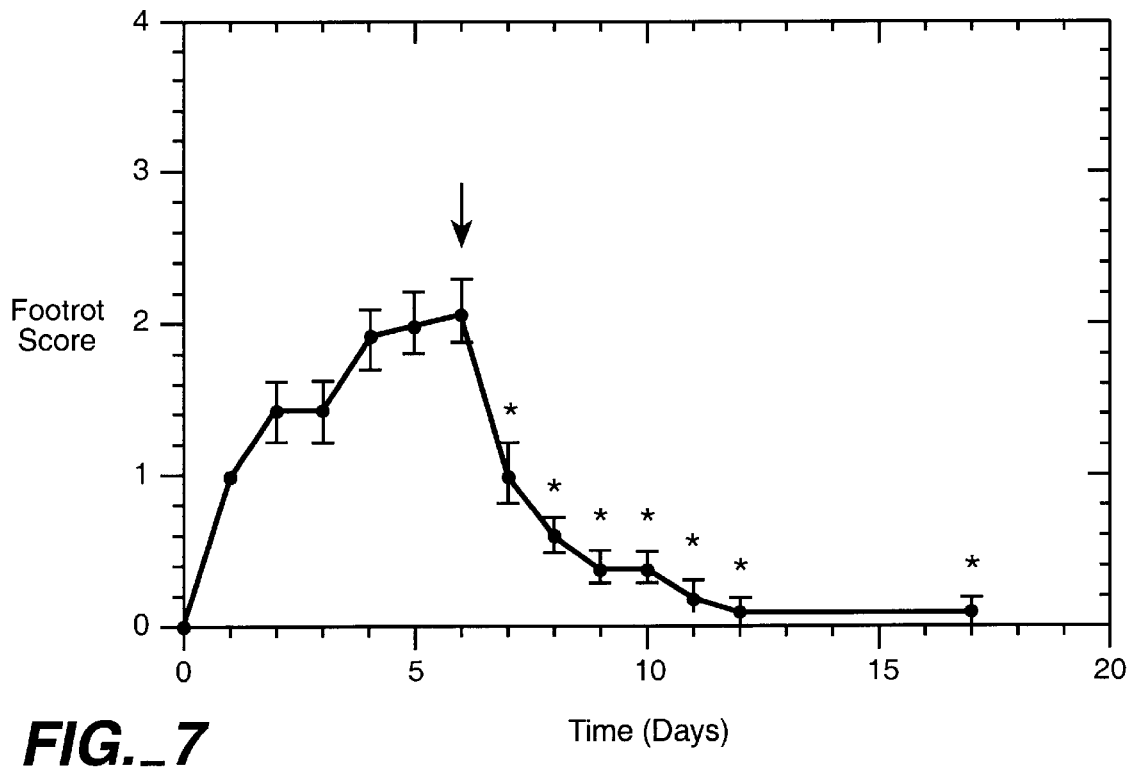
FIG._7
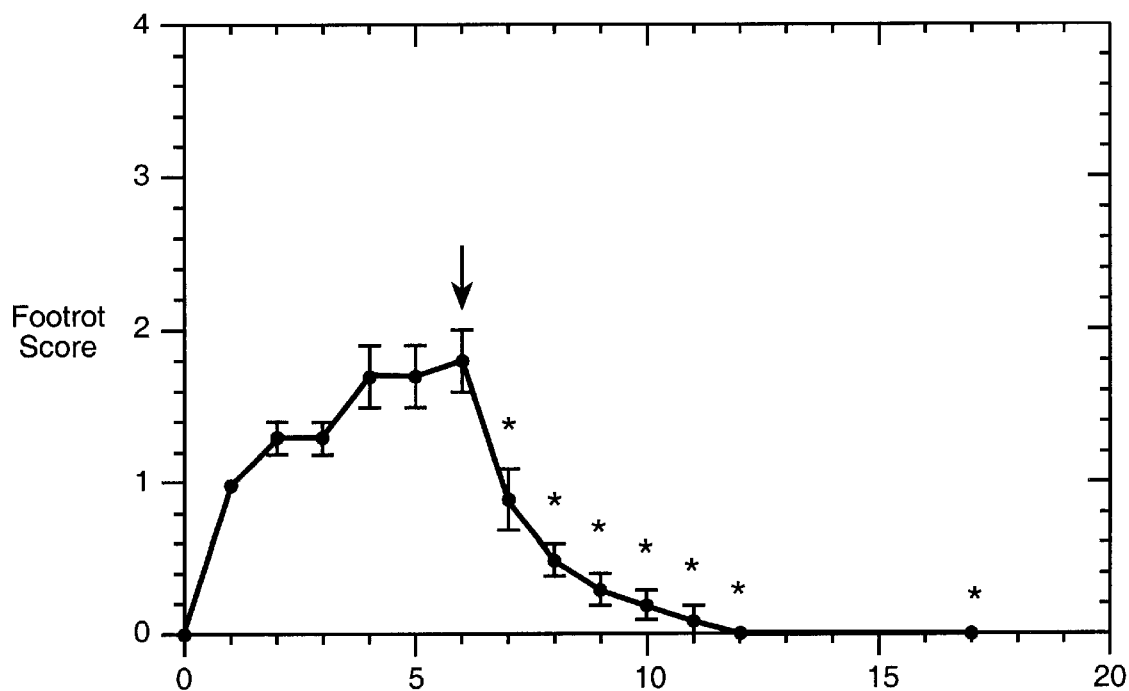
FIG._8

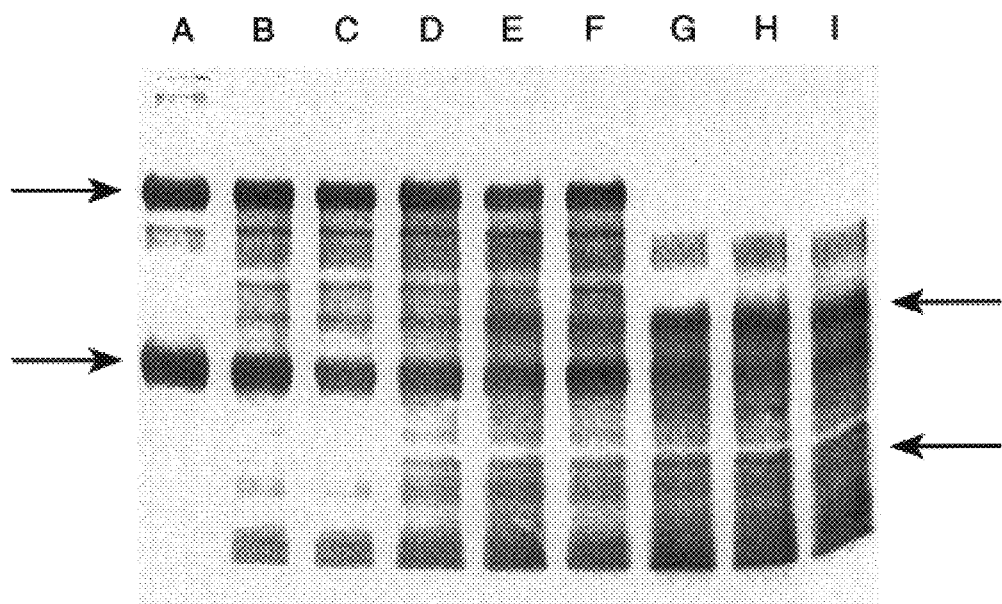
FIG._9A
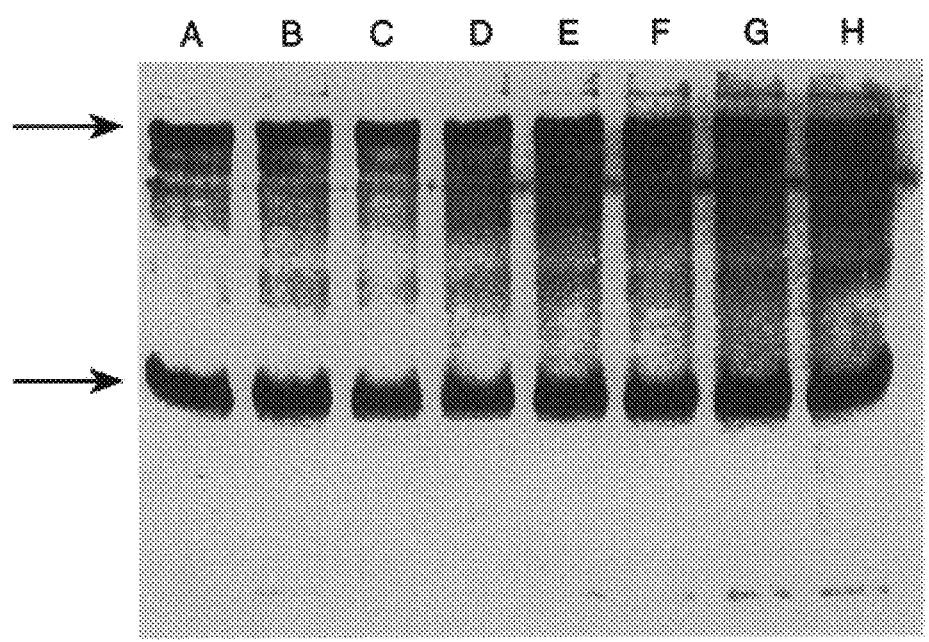
FIG._9B

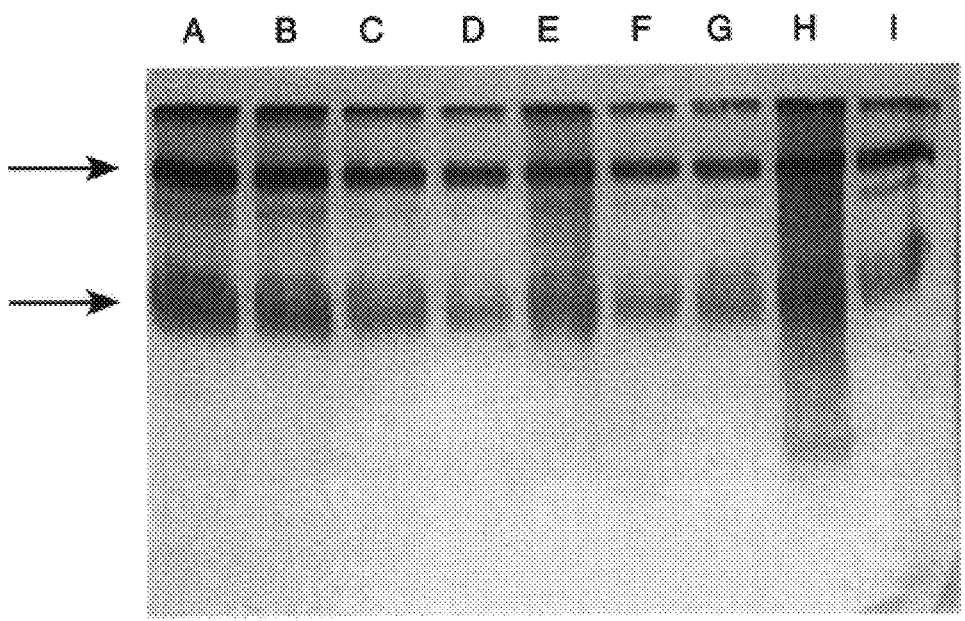
FIG._10A
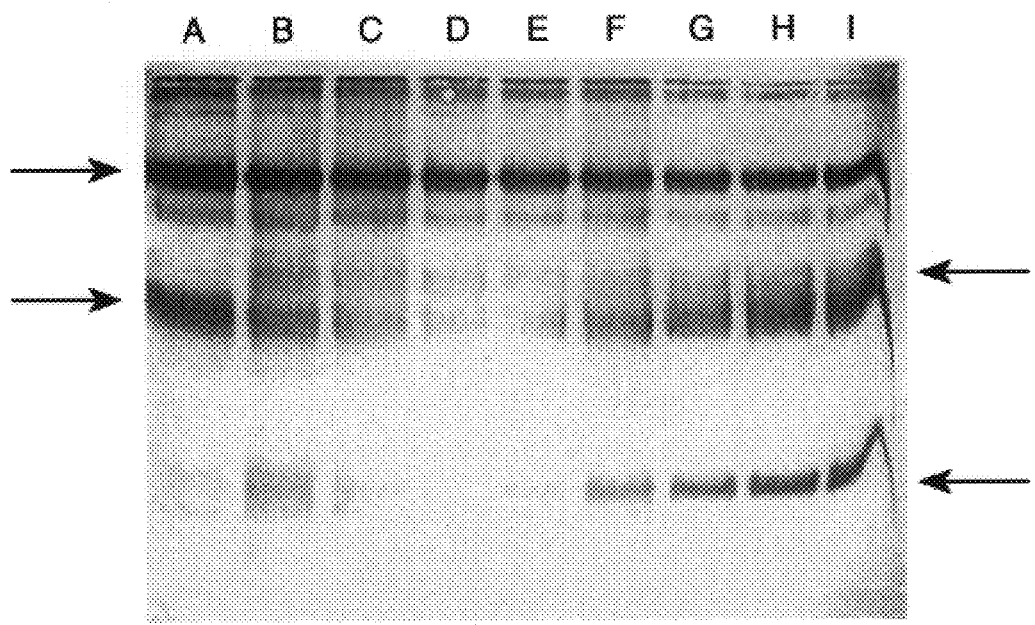
FIG._10B

BOVINE FOOTROT TREATMENT AND PREVENTION

CROSS REFERENCE TO RELATED APPLICATIONS

This application is a divisional of application Ser. No. 09/148,778, filed on Sep. 4, 1998, now U.S. Pat. No. 6,241,992.

This application claims priority to U.S. Application Serial No. 60/058,167 filed Sep. 8, 1997 and U.S. Application Serial No. 60/085,540 filed May 15, 1998. The disclosure of each of these applications is incorporated herein by reference.

FIELD OF THE INVENTION

The present invention relates to compositions useful for the treatment and prevention of footrot and, in particular, bovine footrot.

BACKGROUND OF THE INVENTION

Acute bovine footrot, also known as interdigital phlegmon or acute interdigital phlegmon (AIP), is a common infection in cattle [1,11]. The actual prevalence of this disease in many types of cattle is not fully described; however, in some years the prevalence in feedlot animals can reach 10–25% if preventative measures such as feeding antibiotics are not widely implemented.

It is an anaerobic bacterial infection characterized by acute inflammation which is manifested as tissue edema and local infiltration of subcutaneous tissues with polymorphonuclear granulocytic neutrophils (PMN) [16]. Typically this disease involves necrosis of the interdigital epidermis and the underlying dermis. Very often there is an ascending cellulitis which can result in severe swelling from the coronet to the fetlock joint. This infection, if left untreated, can result in sequelae such as septic joint involvement which can lead to euthanasia [2].

The infection is thought to be caused by a synergistic association of anaerobic bacteria including *Bacteroides melaninogenicus, Fusobacterium necrophorum* [12], and possibly other bacteria such as *Dichelobacter (Bacteroides) nodosus* [13] or *Actinomyces pyogenes* [14]. Recently *B.melaninogenicus* has been divided into several distinct species of bacteria including Porphyromonas sp and Prevotella sp [4]. *Fusobacterium necrophorum* and *B. melaninogenicus* have been previously used together to experimentally infect cattle [12]. That investigation did not examine microscopic pathology or the minimum inhibitory concentrations [MIC's] and minimum bactericidal concentrations [MBC's] of the antibiotic(s) for the pathogens used in the experimental infection.

Several treatments have been advocated for acute bovine footrot including penicillin [11], oxytetracycline [15], cephalosporins [16], and sulfonamides [11].

Parenteral antibiotic treatment of individual clinically affected animals is effective for treating cattle that can be easily handled and frequently observed. Therapy in fat cattle (i.e., animals nearly ready for marketing as beef) is complicated by the fact that many of these drugs cannot be used without delaying slaughter. Antibiotics without withdrawal periods are available for these animals; however, the expense remains significant. Currently, recommended therapy for these animals can involve daily treatment for up to five days or longer. Cephalosporin, a β-lactam antibiotic, is one recommended therapeutic regimen. For a 500 kg steer, cephalosporin therapy for five days can approach $50 in antibiotic cost alone for a single episode of the disease. This clearly does not include the costs of manpower for giving the treatments, the costs of lost production (e.g., reduced weight gain) in affected cattle, or the significant animal suffering that occurs as a result of this infectious lameness.

There are potentially devastating effects of this disease in breeding bulls if the infection occurs during breeding season and libido is reduced. Conventional antibiotic therapy in mature breeding bulls is problematic because of the frequency of treatments and the massive volume of antibiotic required, in addition to the cost of antibiotics. Although infection can be minimized in some types of cattle through feeding antibiotics, fat cattle are again at high risk because of our inability to use these drugs due to withdrawal times. Preventative measures, such as footbaths, are recommended in many parts of the world but are not practical under many circumstances. The potential environmental implications of using compounds such as blue stone and formaldehyde are also a consideration.

Animals affected with AIP are believed to develop immunity, but the importance of this immunity is unclear [2]. In many acute infectious inflammatory diseases phagocytosis by polymorphonuclear granulocytic neutrophils (PMN) is a central mechanism in the resolution of infection, but these cells have never been specifically evaluated in the context of acute bovine footrot. Specific immunity to etiologic agents of footrot also may be important in resolution of the infection [2]; however, studies have yet to be conducted on precisely how these cells are involved in the mechanisms of this process.

The development of a therapeutic agent and/or a vaccine, additional tools for cattlemen to minimize the effects of footrot, would be worthwhile and a significant contribution to sustainable agricultural practices.

Traditionally, *Fusobacterium necrophorum* has been described as the cause of bovine footrot [2–4]. Vaccines based on this microorganism are known and/or available [5,8,9], but efficacy is questionable and use is not broad. Use of 6-substituted 3-nitroimidazo[1,2,b]pyridazine for the control of footrot and liver lesions caused by *Fusobacterium necrophorum* has also been disclosed [10].

SUMMARY OF THE INVENTION

This invention provides a method of preventing or treating bovine footrot by administering vaccine compositions comprising at least one of the causative agents of bovine footrot, i.e., Porphyromonas and Prevotella and/or subunits and/or toxins thereof. Compositions comprising *Porphyromonas levii* and *Prevotella intermedia* are preferred. Protectively immunogenic vaccine compositions may also contain a specific bovine immunoglobulin $G_2$ ($IgG_2$) destroying toxin of *Porphyromonas levii* and a β-lactamase enzyme of *Prevotella intermedia,* either or both of which can be inactivated and included in the vaccine composition. The invention also provides a method of treating or preventing bovine footrot by administering compositions comprising at least one neutralizing agent, e.g., an antibody, to a causative agent of bovine footrot, i.e., Porphyromonas and Prevotella and/or subunits and/or toxins thereof. Compositions comprising antibodies to *Porphyromonas levii* and *Prevotella intermedia* and/or their toxin(s) or subunit(s) are preferred. Effective compositions may contain antibodies to immunoglobulin proteases, including a specific bovine immunoglobulin $G_2$ ($IgG_2$) destroying toxin of *Porphyromonas levii* and/or antibodies to antibiotic resistance enzymes, including a β-lactamase enzyme of *Prevotella intermedia*.

Our isolation techniques and our immunology studies suggest that Porphyromonas (and especially *P. levii*) and Prevotella (and especially *P. intermedia*) are more appropriate vaccine candidates than *Fusobacterium necrophorum*. Using surgical biopsy techniques and stringent anaerobic culture methodology, we have not isolated *Fusobacterium necrophorum* from internal infected tissues in a single case of bovine footrot.

The invention provides compositions and methods for preventing or treating infectious lameness, particularly in cattle, using the bacteria Porphyromonas and/or Prevotella, toxins isolated from these bacteria, and neutralizing agents which may be used in the compositions. The invention provides methods of preparing and methods of using a bacterial protease toxin, an antibiotic destroying toxin, and antibodies to the toxins.

Accordingly, in one aspect, the invention provides compositions for preventing or treating footrot comprising Porphyromonas and/or Prevotella. Compositions comprising subunit(s) and/or toxin(s) of these bacteria are also provided, as are methods of preparing these compositions.

A further aspect of the invention is a method of preventing or treating infection in an animal comprising administering to the animal an effective amount of a composition comprising Porphyromonas and/or Prevotella and/or subunit(s) and/or toxin(s) thereof.

Another aspect of the invention provides isolated toxins from Porphyromonas and/or Prevotella. Methods of preparing the toxins are also provided, as are antibodies to the toxins and a method of passive immunization using the antibodies.

Yet another aspect of the invention provides an experimental model useful for evaluating the effectiveness of possible preventatives or cures for bovine footrot comprising a bovine which has been administered Porphyromonas or Prevotella, especially in conjunction with *Fusobacterium necrophorum*.

In yet a further aspect, the invention provides compositions for preventing or treating footrot comprising at least one agent which neutralizes Porphyromonas and/or Prevotella and/or subunit(s) and/or toxin(s) thereof.

In a still further aspect, the invention provides methods for treating or preventing footrot comprising administering to an animal suffering from or susceptible to footrot an effective amount of a composition which enhances neutrophil-mediated resolution of infection by bacteria associated with footrot.

BRIEF DESCRIPTION OF THE DRAWINGS

FIGS. 1A through 1D are electrophoretic transfers of biotin labeled immunoglobulins that have been incubated with $IgG_2$ destroying toxin-containing extract from *Porphyromonas levii*. In FIG. 1A IgG was used as the immunoglobulin; in FIG. 1B IgM was used; in FIG. 1C $IgG_1$ was used; and in FIG. 1D $IgG_2$ was used. Note that fragments of immunoglobulins are present in FIGS. 1A and 1D, but not in FIGS. 1B and 1C, showing that this protease is $IgG_2$ specific.

FIG. 2 is a photograph illustrating the cefinase method of detecting β-lactamase enzyme. The upper disc is a disc exposed to *Prevotella intermedia*, the lower left disc a negative control, and the lower right disc (marked β) is exposed to commercially purified β-lactamase enzyme-positive control. The results show that *Prevotella intermedia* produces a β-lactamase enzyme.

FIG. 3 is a silver stain SDS-polyacrylamide gel of varying concentrations of protein from a 40–50% ammonium sulfate precipitation of extracts from *Prevotella intermedia*. These extracts retained potent β-lactamase activity as assessed by the cefinase and other assays.

FIGS. 4A through 4C are Western immunoblots of the reaction of bacterial antigens of *Fusobacterium necrophorum* (FIG. 4A), *Prevotella intermedia* (FIG. 4B), and *Porphyromonas levii* (FIG. 4C) with serum collected from cattle experimentally infected with footrot. The results show that animals developed immunity, as evidenced by the development of serum antibodies to *Prevotella intermedia* and *Porphyromonas levii*, but not to *Fusobacterium necrophorum*, after experimental infection.

FIGS. 5A through 5D are Western immunoblots of the reaction of bacterial antigens from *Fusobacterium necrophorum* (FN), *Prevotella intermedia* (5.2), and *Porphyromonas levii* (7.5) with acute serum—taken the day clinical signs were noticed (A); and convalescent serum—taken 28 days after appearance of clinical signs (C) from four animals (FIGS. 5A through 5D) naturally infected with bovine footrot. Note the generally minimal response to *Fusobacterium necrophorum* and the increasing intensity of banding patterns to either *Prevotella intermedia* or *Porphyromonas levii*.

FIG. 6A is a graphical representation of the footrot scores in Group 1 animals (infected with *Porphyromonas levii* and *Fusobacterium necrophorum*). Data are mean scores±standard errors. The arrow indicates the time of treatment and the asterisks represent a statistically significant ($P<0.05$) reduction in footrot score compared to pre-treatment score.

FIG. 6B is a graphical representation of the footrot scores in Group 2 animals (infected with *Prevotella intermedia* and *Fusobacterium necrophorum*). Data are mean scores±standard errors. The arrow indicates the time of treatment and the asterisks represent a statistically significant ($P<0.05$) reduction in footrot score compared to pre-treatment score.

FIG. 7 is a graphical representation of the footrot scores of animals (combined data of Group 1 and Group 2). Data are mean scores±standard errors. The arrow indicates the time of treatment and the asterisks represent a statistically significant ($P<0.05$) reduction in footrot score compared to pretreatment score.

FIG. 8 is a graphical representation of the footrot scores of animals (combined data of Group 1 and Group 2—excluding values from a non-responding animal). Data are mean scores±standard errors. The arrow indicates the time of treatment and the asterisk represents statistical significance compared to pre-treatment score ($P<0.05$).

FIG. 9A is a nitrocellulose transfer of biotinylated IgG exposed to culture supernatant of *P. levii*. From left to right are increasing times (hours) of exposure. Lane A=0, Lane B=0.5, Lane C=1, Lane D=2, Lane E=4, Lane F=8, Lane G=24, Lane H=48, and Lane I=72 h time samples, showing increasing intensity of the degradation bands smaller than the heavy and light chains as incubation time increases and the near complete degradation of the heavy chain by 24 h.

FIG. 9B is a nitrocellulose transfer of biotinylated IgM exposed to culture supernatant of *P. levii*. From left to right are increasing times (hours) of exposure. Lane A=0, Lane B=0.5, Lane C=1, Lane D=4, Lane E=8, Lane F=24, Lane G=48, and Lane H=72 h time samples, showing the absence of degradation bands, with only the light and heavy chains of IgM evident.

FIG. 10A is a nitrocellulose transfer of biotinylated $IgG_1$ exposed to culture supernatant of *P. levii*. From left to right are increasing times (hours) of exposure. Lane A=0, Lane B=0.5, Lane C=1, Lane D=2, Lane E=4, Lane F=8, Lane G=24, Lane H=48, and Lane I=72 h time samples, showing the absence of degradation bands, with only the light and heavy chains of $IgG_1$ being evident.

FIG. 10B is a nitrocellulose transfer of biotinylated $IgG_2$ exposed to culture supernatant of *P. levii*. From left to right are increasing times (hours) of exposure. Lane A=0, Lane B=0.5, Lane C=1, Lane D=2, Lane E=4, Lane F=8, Lane G=24, Lane H=48, and Lane I=72 h time samples, showing the presence of additional bands by 0.5 h, as well as the heavy and light chains of $IgG_2$.

DETAILED DESCRIPTION OF THE INVENTION

The invention is drawn in part to the unexpected discovery that the bacteria Porphyromonas and/or Prevotella, and especially *Porphyromonas levii* and *Prevotella intermedia*, and their subunits and toxins, may be used to prepare vaccine compositions and antibodies useful to prevent and treat bovine footrot. These organisms may also be used as the basis for an experimental model useful for evaluating treatments or preventatives for the disease. The invention is also drawn in part to the discovery that administration of a composition which enhances PMN phagocytosis of the bacteria associated with footrot is a useful method to treat or prevent footrot. Agents which neutralize immunoglobulin proteases and/or the causative organisms of footrot are especially useful.

A. Definitions

As used herein, the following terms have the following meanings:

Adjuvant: a vehicle used to enhance antigenicity. The use of adjuvants is well-known in the art. Adjuvant may include suspensions of minerals on which antigen may be absorbed, such as alum, aluminum hydroxide or phosphate; water-in-oil emulsions in which antigen solution is emulsified in mineral oil, such as Freund's incomplete adjuvant; and may include additional factors, such as killed mycobacteria in Freund's complete adjuvant, to further enhance antigenicity.

Antibody: a molecule, especially a protein, that binds immunologically to a known antigen or a determinant of an antigen. Antibodies are also referred to as immunoglobulins, and are generally classified into isotypes (i.e., IgA, IgD, IgG, IgE and IgM) based on their physicochemical characteristics and amino acid sequence identity. IgA and IgG are further divided into subtypes (i.e., $IgA_1$, $IgA_2$, $IgG_1$, $IgG_2$, $IgG_3$ and $IgG_4$) based on sequence similarity.

Bacterin: the term used to describe vaccines containing killed or inactivated bacteria.

Effective Amount: dose required to protect an animal against infections or disease or alleviate a particular symptom of an infection or disease.

Footrot: also known as interdigital phlegmon, interdigital necrobacillosis, foot abscess, foul-in-the-foot or superfoul. A necrotizing infection of interdigital skin characterized by deep necrosis and fissures. It is associated with infection with either or both of Porphyromonas and Prevotella. The symptoms of the infection, such as lameness, swelling, edema, interdigital lesions, interdigital purulent exudate, etc. are also included in the term footrot.

Immune Response: development in the host of a cellular and/or antibody-mediated immune response to a composition or vaccine of interest. Such a response may consist of one or more of the following: inducing cytokine production, producing antibodies, B cells, helper T cells, suppressor T cells, and/or cytotoxic T cells directed specifically to an antigen or antigens included in the composition or vaccine of interest.

Inactivation: no longer capable of causing disease or a disease condition. Bacteria or bacterial toxins may be inactivated by many known methods. These include, but are not limited to: chemical treatment, e.g., formalin; heat treatment, e.g., mild heating until a toxin is inactivated or cells are killed; attenuation, e.g., making a bacterium or toxin inactive through mutation or genetic/chemical alteration; sonication, e.g., disruption of cells by exposing a suspension of the cells to high frequency sound waves; freezing, e.g., snap freezing cells until they lyse; etc.

Lactamase: also known as β-lactamase. An enzyme or toxin which cleaves a β-lactam structure such as that found in certain antibiotics. This term includes the lactamase produced by *Prevotella intermedia*.

Neutralize: able to prevent or alleviate toxic effects. An agent is a neutralizing agent if it prevents or alleviates the toxic effects of an organism, toxin or subunit. Included in this term are antibodies which bind to an organism, toxin or subunit so as to prevent or inhibit its toxic activity.

Porphyromonas: a genus of anaerobic bacterium that causes bovine footrot. As used in this application, the term includes all species of this genus. The genus Bacteroides, formerly used to refer to as Porphyromonas, is also included in this term as used in this application. In particular, *Porphyromonas levii* was formerly classified as *B. melanogenicus* ssp. *levii*.

Prevention of Symptoms: includes prevention of any effect caused by an infection or disease condition, including effects caused by a toxin.

Prevotella: a genus of anaerobic bacterium that causes bovine footrot. As used in this application, the term includes all species of this genus. The genus Bacteroides, formerly used to refer to Prevotella, is also included in this term as used in this application. In particular, *Prevotella intermedia* was formerly classified as *B. melanogenicus* ssp. *intermedia*.

Production in vitro: production in culture, not in an infected host animal. Production in vitro includes recombinant production.

Protease: an enzyme or toxin which cleaves protein. Proteases may specifically cleave certain proteins, like the $IgG_2$ specific protease produced by *Porphyromonas levii*.

Protectively Immunogenic: able to protect an animal against infection or disease or alleviate particular symptoms of an infection or disease.

Recombinantly Produced: produced by means of gene expression in any other system including microorganisms, plants or animals and/or chemically synthesized by methods known in the art when the gene sequence or amino acid sequence is known.

Resolution of Infection: arrest of infection so as to return to a normal state. Resolution of infection includes resolution of infection mediated by neutrophils, e.g., phagocytosis and oxidative metabolism.

Subunit: any part of a bacterium which is less than the whole organism. Subunits that are antigenic may be used in vaccine compositions to produce an immune response. Subunits may include flagella, pili, fimbriae, membranes, membrane proteins, toxins and any other part of an organism which may be antigenic and induce an immune response. This includes recombinantly produced subunits.

Toxin: a noxious or poisonous substance that is produced by a bacterium. It may be produced and released extracellularly (exotoxin). This includes recombinantly produced toxins.

B. Detailed Description of the Invention

Our studies have shown that during a typical natural clinical infection, humoral and cellular immunity are not strongly developed toward the strains of bacteria involved in natural infections of bovine footrot. Minimal response is seen by Western immunoblot to antigens from these bacteria (i.e., antibodies are poorly produced or readily destroyed). This may be because natural infection does not adequately stimulate the immune system. Alternatively, a normal immune response may be prevented by the infectious agent (e.g., the $IgG_2$ specific protease produced by *Porphyromonas levii*). Neutrophil-mediated resolution of infection includes phagocytosis of infecting bacteria and intracellular destruction of bacteria by oxidative metabolism.

Bacteria have a wide variety of mechanisms for evading or altering an immune response by a host animal. These mechanisms can enable bacteria to more readily establish and maintain an infection. Specifically, it is known that bacterial proteases, and in particular those which cleave immunoglobulins, are one such mechanism. Such proteases may modify important host defenses against bacterial infection. Organisms which produce immunoglobulin proteases include *Proteus mirabilis* [20,21], *Staphylococcus aureus* [22], *Neisseria gonorrhoeae* [23] and *Pasteurella haemolytica* [24]. It is likely that bovine IgG and IgM are the most important classes of immunoglobulins produced by cattle in response to a footrot infection. IgM is the first immunoglobulin recruited against a foreign antigen and IgG has the highest serum concentration. Both are central in immunity during tissue infections [25]. Thus, immunoglobulin protease production by *Porphyromonas levii* is likely an integral mechanism for these bacteria to evade humoral immunity during infection.

Polymorphonuclear granulocytic neutrophils are a central component of acute inflammation in animals [26], including cattle. These cells rapidly, and efficiently, phagocytose most bacteria under normal circumstances. However, we have shown that PMN do not readily phagocytose *P. levii* unless substantial amounts of specific anti-*P. levii* immunoglobulin are present. Thus, in vivo, specific anti-*P. levii* immunoglobulin is crucial for the resolution of infection.

Several types of immunoglobulin can be involved in enhancing phagocytosis by PMN. IgG is composed of two heavy chains, each with a molecular weight of 50 kD, and two light chains, each with a molecular weight of 25 kD. IgM, which has two 65 kD heavy chains and two 25 kD light chains and exists as a pentamer, is a much larger molecule [25]. These immunoglobulin chains form distinct bands at their respective molecular weights upon SDS PAGE treatment. We have found the presence of bands at other locations after incubation with culture supernatant containing *P. levii* protease, showing that these protein chains have become fragmented. The results of our studies show that *P. levii* produces an enzyme which specifically cleaves $IgG_2$, but not $IgG_1$ or IgM.

The description of a *P. levii* protease which is IgG specific is significant because such a protease may aid in the establishment of these bacteria during an infection by cleaving specific IgG which could potentially aid in clearance of the infection. In the bovine animal $IgG_2$ is the most important antibody in neutrophil-mediated phagocytosis [6] and in antibody dependent cell mediated cytotoxicity [27]. Antigen coated with $IgG_1$ are not readily adhered to by neutrophils or phagocytosed by these leukocytes. $IgG_2$ has also been shown to mediate phagocytosis by peripheral blood monocytes to a greater extent than $IgG_1$, and IgM failed to do so without complement addition. Thus, the action of neutrophils is an important factor in the clearance of *P. levii* infection in the bovid. By producing a protease which specifically cleaves $IgG_2$ and inhibiting neutrophil-mediated phagocytosis, the organism increases its opportunities to create a viable infection in the bovine foot because the inability to successfully phagocytose infecting bacteria can compromise the host and aid in the progression of this infection. Thus, administration of an agent which neutralizes this protease will enhance neutrophil-mediated phagocytosis and speed resolution of the infection by the host.

The *P. levii* protease appears to function optimally at 35° C., a temperature not unlike that of the distal bovine limb. The specificity of this protease activity suggests that the enzyme may act specifically at the hinge region of the immunoglobulin. Such a region is not present in IgM and is the area with the highest degree of variance between $IgG_1$ and $IgG_2$ [28,29]. The near complete disappearance of heavy chain from the IgG preparation under conditions of lengthy incubation suggests that multiple enzyme activities are occurring and that the degradation of these Igs is complex.

In natural infections, neutrophils (cells that kill bacteria), but very few lymphocytes, are recruited to the area of infection. Under optimal circumstances, neutrophils can resolve the infection through phagocytosis (ingestion and destruction of the offending bacteria). It is well known that a $Th_1$ (T-helper lymphocyte 1) response and the associated $IgG_2$ that is produced by a $Th_1$ response, is critical for neutrophils to destroy bacteria by phagocytosis [6]. We have demonstrated that bacteria causing footrot (*Porphyromonas levii*) produce a specific toxin (a protease) that destroys only $IgG_2$ (see FIGS. 1A through 1D). This toxin may act in the foot of affected cattle to destroy the $IgG_2$ crucial for successful resolution of the infection by neutrophils. The use of this toxin in a vaccine composition will result in formation of antibodies which can neutralize or inhibit the toxin before it destroys $Th_1$ associated $IgG_2$, thus allowing the neutrophils to phagocytize the bacteria.

Others [7] have postulated that immune responses can be altered and tailored to specific conditions (such as a $Th_1$ or a $Th_2$ response) through the strategic delivery of cytokines (immune messenger molecules). Such a tailored delivery of a vaccine may be useful in bovine footrot, where it would be useful to increase $IgG_2$ production to overcome the effects of the *Porphyromonas levii* protease toxin.

Bovine PMN efficiently phagocytosed *P. intermedia* and *F. necrophorum,* but not *P. levii*. High titre anti-*P. levii* serum increased the efficiency of phagocytosis of *P. levii* and this increase in phagocytosis was independent of heat labile complement components. *Porphyromonas levii* produced an Ig protease which cleaves bovine IgG, but not IgM. We postulate this specific humoral immunity may be involved in the resolution of this infection. *Porphyromonas levii* produces a protease that was found to cleave $IgG_2$, the Ig class involved in PMN-mediated phagocytosis, but not $IgG_1$ or IgM. This enzyme is, thus, a significant virulence factor in AIP through local inhibition of immunoglobulin assisted PMN-mediated phagocytosis.

We have discovered in our PMN phagocytosis studies that the action of neutrophils is an important factor in the clearance of *P. levii* infection in the bovid affected with acute interdigital phlegmon. By producing a protease, or possibly several proteases, which act alone or collectively to specifically cleave $IgG_2$ and therefore inhibiting PMN-mediated phagocytosis, *P. levii* increases its opportunities to create a viable infection in the bovine foot. The inability to successfully phagocytose these bacteria could compromise the host and aid in the progression of this infection. Thus, agents which neutralize such protease are useful to treat footrot.

Studies from our laboratory show that PMN chemotactically move toward bacteria associated with acute footrot in an efficient manner, demonstrating that their motility is unaffected by these bacteria. Results are presented in Table A. Chemotaxis is the movement of cells (here, PMN's) along a concentration gradient of the agent, while chemokinesis is the movement of PMN along a gradient of serum.

TABLE A

Neutrophil Chemotaxis and Chemokinesis

| Stimulus | Chemotaxis (μm/h) | Chemokinesis (μm/h) |
|---|---|---|
| Negative Control | 11.2 + 0.5 | 94.1 + 5.6 |
| Positive Control | 24.8 + 0.9 | 121.4 + 1.5 |
| P. levii | 22.8 + 2.1 | 122.6 + 1.8 |
| P. intermedia | 29.7 + 2.0 | 80.7 + 2.3 |
| F. necrophorum | 44.8 + 1.0 | 99.3 + 2.3 |
| All 3 Bacteria | 32.1 + 2.3 | 110.7 + 2.8 |

Additionally, we have found that PMN demonstrate significant oxidative metabolism when exposed to *P. levii* or *F. necrophorum*, but that the percentage of PMN which are oxidatively metabolic decreased when exposed to *P. intermedia*. Thus, decreasing oxidative metabolism of PMN by *Prevotella intermedia* is likely an integral mechanism for these bacteria to evade host resolution of infection. Results are presented in Table B.

TABLE B

PMN Oxidative Metabolism

| Experimental Group | % PMN Oxidatively Active (Mean ± SE) n = 9 |
|---|---|
| Resting | 10.0 ± 0.6 |
| Stimulated (PMN) | 94.0 ± 0.5 |
| F. necrophorum | 80.8 ± 1.2 |
| P. levii | 82.8 ± 0.7 |
| P. intermedia | 18.3 ± 0.7 |

*Prevotella intermedia* also produces a toxin (a β-lactamase enzyme) that destroys certain antibiotics, i.e., those which contain a β-lactam ring structure, such as penicillins and cephalosporins (FIG. 2). This enzyme has been partially purified by precipitating the enzyme in 40–50% ammonium sulfate (FIG. 3). Use of this enzyme in a vaccine composition will result in raising antibodies against the enzyme which inactivate its activity. This will allow more efficient use of antibiotics, even β-lactam antibiotics, to treat the infection.

We have shown via immunoblots with acute and convalescent sera of experimentally infected animals that one can successfully immunize cattle with antigens of Porphyromonas and Prevotella (FIGS. 4A through 4C). Acute and convalescent sera from some feedlot steers with footrot show rising titers to these antigens (FIGS. 5A through 5D), but the reaction is not as strong as that seen in experimentally infected steers. These Western blots indicate that antibodies are weakly or not at all produced against *Fusobacterium necrophorum*, further supporting a minimal role for this bacterium in the disease.

Moreover, histological assessment of experimentally infected feet indicates that predominantly macrophages (phagocytic and antigen presenting cells) and lymphocytes (antibody producing and processing cells that coordinate immunity) are present. These data show that Porphyromonas and Prevotella vaccine compositions provide effective humoral and cellular immune responses against footrot-causing organisms. Pre-exposure vaccination with vaccine compositions prepared from these organisms and/or their subunits and/or toxins provide antibody, immune memory cells, and other specific lymphocytes which will alter the course of infection through enhancing the function of neutrophils. The most effective treatment must negate the activities of the *Porphyromonas levii* $IgG_2$ toxin to allow neutrophil destruction of bacteria.

This invention provides vaccine compositions comprising the footrot causing bacteria Prevotella and Porphyromonas. It has been found, using surgical biopsy methodology to obtain specimens from bovine footrot, that these bacteria, and not *Fusobacterium necrophorum* which was traditionally thought to cause bovine footrot, are the causative agents of footrot. We have used these bacteria, grown under strictly anaerobic conditions in the laboratory, in the presence of haemin and Vitamin K, to vaccinate animals. Further, we are able to produce and isolate bacterial toxins from in vitro cultures of these bacteria. These toxins can be used for protective immunization against infection by the bacteria causing bovine footrot or for raising toxin neutralizing antibodies for use in passive immunization of affected animals.

In particular, *Porphyromonas levii* and *Prevotella intermedia*, which are present in the cellulitic tissues of animals affected with bovine footrot, are preferred for use in the present invention. In a most preferred embodiment, the invention provides inactivated bacteria, toxins, and antibodies to toxins and antigens of *Porphyromonas levii* and *Prevotella intermedia*. Such inactivated bacteria, toxins, and antibodies are useful for preventing and treating bovine footrot and the symptoms thereof.

A variety of strains of Porphyromonas and Prevotella are useful in the present inventions. Strains which grow well in vitro, are able to infect the target animal species, and produce toxin when grown in vitro, are preferred. The bacterial strains used in this invention are cultured by growing them in appropriate media, e.g., bovine tissue based medium, such as chopped meat medium or brain heart infusion medium that has been supplemented with haemin and Vitamin K, with resazurin as an indicator, under conditions of strict anaerobiasis.

The invention also provides compositions comprising inactivated Prevotella and/or Porphyromonas bacteria which compositions are protectively immunogenic. Various strains of Prevotella and Porphyromonas bacteria may be useful in such vaccine compositions. Vaccine compositions may contain one or more of the bacteria causing bovine footrot, and/or one or more subunits and/or toxins of these bacteria. *Porphyromonas levii* and *Prevotella intermedia* are preferred. In particular, strains of *Porphyromonas levii* and *Prevotella intermedia* which produce large amounts of toxin when cultured in vitro are most preferred.

The bacterial strains may be cultured as set forth in the Examples below, then harvested for use in vaccine compositions. Bacteria are preferably inactivated before use in vaccine compositions. Various methods of disruption may be preferably used to inactivate the bacteria, including sonication, osmosis, use of pressure differentials or freezing. Freezing is the most preferred. Conventional techniques such as mild heat treatment or formalin inactivation may also be used to inactivate bacteria or toxins used in vaccine compositions.

The formulation of such vaccine compositions may include suitable pharmaceutical carriers, including adjuvants. The use of an adjuvant, such as an alum-based adjuvant is preferred. Many commercial adjuvants may be useful in the present invention. For these studies an alum-based adjuvant containing aluminum hydroxide (Inject Alum, Rockford, Ill.) was used. Exact formulation of the vaccine compositions will depend on the particular formulation and the route of immunization. Such vaccine composition formulation is well-known to those skilled in the art [30].

Such vaccine compositions are useful for immunizing any animal susceptible to footrot. The present invention provides a method of preventing or treating footrot by administering an effective amount of a vaccine composition of Prevotella and/or Porphyromonas to an animal in need of such prevention or treatment. Bovines are preferable treated. In particular, preferred vaccine compositions comprise *Porphyromonas levii* and/or *Prevotella intermedia*.

The invention further provides compositions comprising neutralizing agents, such as antibodies, to Prevotella and/or Porphyromonas bacteria and/or their toxins or subunits, which compositions are useful to treat footrot. Formulation of such compositions may include suitable pharmaceutical carriers, and is also well-known to those skilled in the art.

The route of administration may be any convenient route, and may vary depending on the particular bacteria, subunit, toxin or agent used in the composition, the animal to be treated and/or vaccinated, and other factors known to those of skill in the art. Parenteral administration, such as subcutaneous, intramuscular, or intravenous administration is preferred. Subcutaneous administration is most preferred for food-producing cattle. Oral administration may be used, including oral dosage forms which may be enteric-release coated. Intraperitoneal, nasal and rectal routes of administration are also contemplated.

The schedule of administration may vary depending on factors such as the bacteria and the animal being treated. Animals may receive a single dose, they may receive an initial dose and a booster dose, or they may receive multiple doses. Annual boosters may be used for continued protection. In particular two doses 21 days apart are preferred as a primary course. Development of such schedules of administration is known to those of skill in the art.

The age of the animal to be treated may also affect the route and schedule of administration. For example, for vaccination, administration is preferred at an age when maternal antibodies are no longer present and the animal is immunologically competent. This is about 2–4 months of age in cattle. Additionally, administration of vaccine composition to mothers so that they develop antibodies is useful to prevent infection of their offspring through passive transfer of antibodies in colostrum and milk.

The methods of this invention are effective in preventing colonization of the subcutaneous tissues of the foot with bacteria which cause bovine footrot. They are also effective in preventing the symptoms of bovine footrot. This includes neutralization of toxin and prevention of the physiological effects of toxin which may occur when Porphyromonas and/or Prevotella are present in the foot of the animals.

Treatment may be administered to symptomatic or asymptomatic animals, including animals with chronic infection. Inducing the production of neutralizing antibody against Porphyromonas protease toxin or delivering antibody or another agent which neutralizes this toxin allows natural development of neutrophil associated antibody that provides successful recovery from infection with footrot causing organisms such as Porphyromonas and/or Prevotella. Such antibodies or other neutralizing agents will also allow development of antibodies to other organisms (such as *Fusobacterium necrophorum*) which may be associated with footrot.

The present invention also provides toxins of *Porphyromonas levii* and *Prevotella intermedia* and methods of producing these toxins. It has been found that these organisms, when cultured in medium with haemin and Vitamin K under anaerobic conditions, produce certain toxins in vitro. These toxins may be used to immunize animals against footrot. The toxins may be isolated from the supernatants of the bacterial cultures. They are useful for preventing and treating infection.

Supernatants from the cultured bacteria (*Porphyromonas levii*) contain a toxin (protease) that specifically cleaves bovine $IgG_2$ into fragments. Isolated toxin was incubated with biotin-labeled immunoglobulin and the resulting mixture separated by SDS PAGE. When active toxin was present, $IgG_2$ fragments were produced as the toxin cleaved the immunoglobulin. Immunoglobulins remained intact when no toxin was present or when the toxin was purposely inactivated. The toxin was also shown not to be active against other immunoglobulins (i.e., $IgG_1$ and IgM). FIGS. 1A through 1D present these results.

Supernatants from the cultured bacteria (*Prevotella intermedia*) contain a toxin (β-lactamase enzyme) that specifically cleaves β-lactam antibiotics. See FIG. 2. This toxin has been purified using ammonium sulfate precipitation methods.

The present invention also provides antibodies to Prevotella and Porphyromonas and/or their toxins or subunits. Polyclonal and monoclonal antibodies may be raised by conventional techniques. These antibodies will be useful to enhance neutrophil-mediated phagocytosis and as an antiserum to neutralize the effects of toxin. Thus, when administered to an animal, e.g., intravenously, they may be expected to relieve symptoms of bovine footrot.

Two strains of anaerobic bacteria, *Porphyromonas levii* and *Prevotella intermedia*, were assessed for their ability to induce acute footrot in cattle. They were used in conjunction with *Fusobacterium necrophorum*. Cattle feet were experimentally infected with these bacteria and animals were examined clinically, histopathologically, and bacteriologically for response to inoculation with these anaerobic bacterial species. After experimental induction of footrot, response to a macrolide antibiotic to evaluate its potential usefulness as a footrot treatment was examined. *Porphyromonas levii* caused a significantly more severe infection than *Prevotella intermedia,* as assessed by clinical scoring, when inoculated into the bovine interdigital space. Histological examination of affected tissue demonstrated local edema, necrosis, infiltration of the subcutaneous tissue with leukocytes, and bacterial cells morphotypic of the strains used to infect the interdigital tissues. In all cases bacteria recovered from biopsy samples of the infected feet six days following experimental infection were consistent with those strains initially injected into the animals. MIC's and MBC's of bacteria used to infect feet were not different from the MIC's and MBC's of bacteria recovered from the feet six days later, but prior to therapy. All animals were treated with antibiotic on the sixth day following the experimental infection and 83.3% (⅚) responded very favorably to this treatment, based on a subjective assessment of the severity of lameness, swelling, and lesions.

Cattle injected in the interdigital skin and subcutaneous tissue with *Porphyromonas levii* or *Prevotella intermedia,* together with *Fusobacterium necrophorum,* developed a clinical condition consistent with acute footrot within five days, causing interdigital necrosis, swelling of the interdigital tissues and distal subcutaneous tissue, and lameness. This experimental model resulted in lesions and lameness typical of the natural infection in cattle. Histopathological features (edema, leukocyte infiltration, necrosis) in the subcutaneous tissues were also typical of natural infection. All of these findings are considered characteristic of acute footrot. We have demonstrated that *Porphyromonas levii* or *Prevotella intermedia* inoculated into the interdigital skin of cattle can induce acute footrot, in particular when injected in conjunction with *Fusobacterium necrophorum*.

This experimental model infection system is useful to further examine the pathophysiological and immunological consequences of acute bovine footrot and is a useful screening tool for the evaluation of potential new therapeutics for footrot, such as antibiotics and vaccines. Based on these results, it appears that the macrolide antibiotic we tested is a useful antibiotic for the treatment of acute bovine footrot.

C. Examples of Embodiments of the Invention

The following examples are not intended to limit the scope of the invention in any manner. In general the following materials and methods were used in the examples unless otherwise noted:

1. Medium Preparation.

The medium used for culture of the *Porphyromonas levii* and *Prevotella intermedia* (Brain Heart Infusion broth with haemin and Vitamin K and resazurin) was prepared as indicated below.

| Medium Component | g/l |
| --- | --- |
| Calf brains, infusion from | 200 g |
| Beef heart, infusion from | 250 g |
| Bacto protease peptone | 10 g |
| Bacto dextrose | 2 g |
| Sodium chloride | 5 g |
| Disodium phosphate | 2.5 g |
| Hemin | 5 mg |
| Vitamin K | 1 mg |
| Resazurin | 1 mg |

2. Biopsy Isolation of *Porphyromonas levii* and *Prevotella intermedia*.

The foot of a bovine with clinical footrot was lifted and cleaned using water and disinfectant solution followed by 70:30 (vol/vol) ethanol:water. A small incision was made using a scalpel blade (#10) over a swollen portion of the limb immediately proximal to the affected region of the foot. A Trucut™ hepatic biopsy needle was inserted into the subcutaneous tissue. A core of tissue was collected, placed in pre-reduced transport medium (Anaerobe Systems, San Jose, Calif.) and transported immediately to the laboratory in anaerobic transport medium.

*Porphyromonas levii* and *Prevotella intermedia* were grown separately on kanamycin:vancomycin laked blood agar and Brucella blood agar for five days under conditions of 5%$H_2$:5%$CO_2$:90%$N_2$ at 37° C. A single colony of each organism was inoculated into a separate tube of modified chopped meat medium and grown for 24 h at 37° C. in an anaerobic chamber.

3. Freezing *Porphyromonas levii* and *Prevotella intermedia*.

The isolated bacteria were kept frozen at −85° C. in either pre-reduced transport medium or semisolid BHI broth under anaerobic conditions.

4. Growing *Porphyromonas levii* and *Prevotella intermedia*.

Both bacterial species were grown in supplemental BHI broth (above). Broths were inoculated from secondary cultures that have been expanded from primary cultures stored in the laboratory. Bacteria were incubated at 37° C. in an anaerobic atmosphere (5% carbon dioxide, 5% hydrogen, balance nitrogen). Broths of *Porphyromonas levii* were incubated 96 h and *Prevotella intermedia* broths were incubated 72 h.

5. Harvesting *Porphyromonas levii* and *Prevotella intermedia*.

Bacteria were harvested by centrifugation at 3000×g for 10 min. Pellets were resuspended and washed three times in sterile PBS.

6. Preparing Vaccine from *Porphyromonas levii* and *Prevotella intermedia*.

To lyse cells the washed bacteria were snap frozen in liquid nitrogen, thawed, and snap frozen again. Protein concentration was determined by the Bradford protein assay and vaccines were stored at −20° C. until needed.

EXAMPLE 1

Immunological Assessment of Animals Naturally Infected with Bovine Footrot

To assess the humoral immunity (antibody production) resulting from natural infection with bovine footrot, acute and convalescent sera were obtained from affected animals. Acute serum was collected via jugular venipuncture on the day an animal initially showed clinical signs of acute bovine footrot (i.e., lameness, swelling of the interdigital region and distal foot, and/or a necrotic lesion of the interdigital space). Twenty-eight days following appearance of clinical signs, a second (convalescent) sample was collected, also by jugular venipuncture. Serum was separated from cells and stored at −85° C. until used in the Western blotting assays.

*Porphyromonas levii* (7-5) was grown on Brucella blood agar and inoculated into pre-reduced chopped meat medium with Vitamin K, hemin and resazurin and grown anaerobically (5% $H_2$:5%$CO_2$:90%$N_2$) for 24 h. *Prevotella intermedia* (5-2) was grown under similar conditions for 48 h and *Fusobacterium necrophorum* ATCC 27852 (ovine footrot isolate) was grown for five days on chocolate agar under similar conditions, inoculated into modified chopped meat medium and grown anaerobically for 24 h. Bacteria were harvested by centrifugation (5000×g for 15 min) and the pellets placed in frozen aliquots. Protein concentrations of these aliquots of centrifuged bacterial cells following a freeze-thaw were determined by the Bradford protein assay.

Sodium dodecyl sulfate polyacrylamide gel electrophoresis (SDS PAGE) was conducted on these bacterial specimens (10 μg protein per lane) following boiling in SDS PAGE reducing and denaturing sample buffer according to accepted methodology [31]. Electrophoretically separated proteins within the gel (4% stacking gel and 12% resolving gel) were electrophoretically transferred to nitrocellulose paper (18 h at 4° C. and 30V) according to accepted methodology [32]. Protein transfer was confirmed by amido black staining of a strip of nitrocellulose paper. Strips were blocked with 1% skim milk in Tris buffered saline and exposed to either acute serum or convalescent serum from cattle with footrot. Sera were used at the same dilution (1:200). A monoclonal antibody raised against bovine IgG (heavy chain specific) conjugated to alkaline phosphatase was used as a detection method for bound bovine IgG. Color reaction involved incubation of nitrocellulose strips with nitro blue tetrazolium in 0.2M Tris-HCl 4 mM $MgCl_2$ pH 8.8 buffer with 5-bromo-4-chloro-3-indolyl phosphate in dimethyl sulfoxide. Development of blots proceeded for exactly 10 min and the development reaction was stopped with ice water. Blots were immediately photographed.

Western blotting results from four animals are shown in FIGS. 5A through 5D. In each figure, the acute (A) and convalescent (C) serum reactions are shown against the antigens from *Fusobacterium necrophorum* ATCC 27852, *Prevotella intermedia* (5.2) and *Porphyromonas levii* (7.5). In animal 42030R (FIG. 5A), increased titers of IgG antibodies against *Prevotella intermedia* (5.2) and *Porphyromonas levii* (7.5) were seen in convalescent serum relative to acute serum. Only a slight increase in antibody titer was seen with *Fusobacterium necrophorum* ATCC 27852. In animals 1875RED (FIG. 5B), 2281GRN (FIG. 5C), and PUR01 (FIG. 5D), no rising titers of IgG against *Fusobacterium necrophorum* were detected, but increasing IgG titers to one or both of *Prevotella intermedia* or *Porphyromonas levii* were clearly observed. This is evidenced by the increasing number and intensity of the protein bands observed on the strips in the convalescent sera samples. These data show that over the 28-day period in which the animals recovered from the disease, a specific immune response was produced against *Prevotella intermedia* (5.2) and/or *Porphyromonas levii* (7.5), but no substantive production of IgG specifically reactive to *Fusobacterium necrophorum* was detected. These data indicate *Fusobacterium necrophorum* is not immunologically recognized by the host. They also indicate that *Prevotella intermedia* and/or *Porphyromonas levii* are important agents in the disease, and that a comparatively weak (1:200 dilutions) serum IgG response is produced toward these bacteria in the course of natural infection.

EXAMPLE 2

Immunological Assessment of Animals Experimentally Infected with Bovine Footrot

To assess the humoral immunity (antibody production) resulting from experimental infection with bovine footrot, pre-exposure serum, acute serum, and convalescent sera were obtained from animals experimentally infected with bovine footrot as described in Example 5 below. Pre-exposure serum was collected prior to infection by jugular venipuncture. Acute serum was collected by jugular venipuncture on the day following experimental infection and a second (convalescent) sample was collected, also by jugular venipuncture, 11 days following infection. Serum was separated from cells and stored at −85° C. until used in the Western blotting assays.

*Porphyromonas levii* (7-5), *Prevotella intermedia* (5-2) and *Fusobacterium necrophorum* ATCC 27852 (ovine footrot isolate) proteins were prepared as described in Example 1.

Western blotting results (performed as described in Example 1) from a steer experimentally infected with *Porphyromonas levii* and *Fusobacterium necrophorum* are shown in FIGS. 4A through 4C. In FIG. 4A the antigen used was *Fusobacterium necrophorum* ATCC 27852. The results shown in FIG. 4A clearly demonstrate that levels of IgG against *F. necrophorum* are negligible at all time periods tested—pre-exposure, acute exposure and convalescent exposure. Conversely, this animal showed rising IgG titers to both *Prevotella intermedia* 5.2 (FIG. 4B) and *Porphyromonas levii* 7.5 (FIG. 4C), indicating some shared antigenicity between *Prevotella intermedia* 5.2 and *Porphyromonas levii* 7.5. The negligible immune response to *Fusobacterium necrophorum* suggests that it is not readily recognized by the host immune system and/or that it is not involved in the active infection of the subcutaneous tissues in footrot.

Four of the six experimentally infected animals were re-assessed as above approximately eight weeks following experimental infection to determine the presence of serum IgG specific for whole bacterial cell extract antigens. The pattern of serum IgG remained the same. This demonstrates that the serum IgG produced in response to experimental infection lasts for a minimum of several weeks and similar lasting serum IgG may be created via vaccination. The data show that, despite the known presence of *Fusobacterium necrophorum* within experimentally infected tissue, no substantial immunological response to this bacterium occurs in experimentally infected cattle, while *Prevotella intermedia* and/or *Porphyromonas levii* are the important etiologies of the disease.

EXAMPLE 3

Production and Assessment of Immunoglobulin G2 Destroying Toxin

N-hydroxy-succinomidobiotin (Sigma Biosciences, St. Louis, Mo.) was dissolved in dimethyl sulfoxide to a 1 mg/ml concentration. It was then added to equal one tenth the weight of bovine IgG (Sigma Biosciences, St. Louis, Mo.), IgM (Sigma Biosciences, St. Louis, Mo.), $IgG_1$ (Chemicon International, Inc., Temecula, Calif.) and $IgG_2$ (Chemicon International, Inc., Temecula, Calif.). The solution was then incubated for 2 h at 25° C. and the reaction stopped with 1 mg of glycine (Sigma Biosciences, St. Louis, Mo.). The biotinylated immunoglobulins were dialyzed overnight in three changes of double distilled water. Final concentrations were 10 mg/ml for IgG, $IgG_1$ and $IgG_2$ and 1.1 mg/ml for IgM.

Supernatant of a broth culture of *P. levii* grown in anaerobic conditions (5% $H_2$:5% $CO_2$:90% $N_2$) in Cooked Meat broth (BBL, Cockysville, Md.) (supplemented with 5 mg/l of hemin, 1 mg/l of Vitamin K and 1 mg/l resazurin (Sigma Biosciences, St. Louis, Mo.) at 37° C. for four days was collected by centrifugation. The bacterial culture was centrifuged at 3020×g for 20 min to remove bacterial cells. The remaining supernatant was placed in aliquots of 250 μl amounts for the protease assay. Culture purity was assured by streak plating onto Brucella Blood Agar and standard bacteriological identification.

Procedures were slight modifications of the methods of Lee and Shewen [24]. Ten microliters of biotinylated immunoglobulin was added to 250 μl of bacterial culture supernatant and 2.5 μl of penicillin-streptomycin solution. The mixture was incubated at 35° C. and 10 μl samples taken at 0, 0.5, 1, 2, 4, 8, 24, 48, and 72 h. The samples were added to a 10 μl of sample buffer, boiled for 4 min and analyzed by SDS PAGE, electrophoretic transfer and streptavidin-alkaline phosphatase exposure. Controls included *P. levii* supernatant heated to 100° C. prior to exposure to the biotinylated Igs and uninoculated culture supernatant.

All samples were loaded onto 15% resolving gels with 4% stacking gels for SDS PAGE using standard methodology [31]. Gels were run on ice at 150V for 15 min and at 200V for 45 min in 10% running buffer. The proteins in the gel were then transferred to nitrocellulose paper using standard methods [32]. Transfer was at 20V overnight at 4° C. Blocking was conducted using a 1 h incubation at 37° C. in a solution of skim milk powder (2% wt/vol) and Tris buffered saline containing Tween 20 (18 g NaCl, 2.42 g Trizma base, 2 l double distilled water, 1 ml Tween 20, pH 7.4) (TBS-tween). Blots were washed with TBS-tween three times (15 min) at room temperature, then incubated in a 1:5000 dilution of streptavidin-alkaline phosphatase (Sigma Biosciences, St. Louis, Mo.) in TBS-tween for 2 h at 37° C.

The blots were again washed three times for 15 min in TBS-tween. Nitroblue tetrazolium (Sigma Biosciences, St. Louis, Mo.) (NBT) and 5-bromo-4 chloro-3 indolyl phosphate (Sigma Biosciences, St. Louis, Mo.) (BCIP) were added as substrate for color development, which was allowed to proceed for 4 min. Substrate solution was composed of 10 mg of NBT dissolved in 100 ml of developing buffer (31.52 g Tris-HCL, 0.18 g $MgCl_2$-$6H_2O$, 1 l distilled water, pH 8.8) and 5 mg of BCIP dissolved in 1 ml of dimethyl sulfoxide was added to this solution. Protein bands representing the light and heavy chains of the biotinylated immunoglobulins, or fragments of these immunoglobulin chains were viewed based on alkaline phosphatase activity on the nitrocellulose paper. Photographs were obtained immediately.

Assays performed on biotinylated IgG produced degradation bands, fragments of the immunoglobulin heavy and light chains, by 0.5 h, as seen in FIG. 1A. The intensity of these Ig fragment bands continued to increase during the 72 h of incubation. Optimization studies performed on IgG showed that incubation of the supernatant with IgG at 35° C. showed the most pronounced activity and that a streptavidin-alkaline phosphate dilution of 1:5000 gave optimal results. All further assays were performed under these same conditions. When IgM was examined using these methods (FIG. 1B) there were no degradation bands (immunoglobulin fragments) formed. Only bands representing intact heavy and light chains of IgM could be visualized. When $IgG_1$ was assayed, degradation bands were not evident (FIG. 1C) and again only bands representing intact heavy and light immunoglobulin chains could be recognized. However, when assays using $IgG_2$ were conducted results similar to those performed with mixed subtype IgG were seen. Degradation bands were evident within 30 min, as demonstrated in FIG. 1D. Controls using heated supernatant and uninoculated media, each of which was exposed to the biotinylated bovine IgG, showed no evidence of degradation bands. This indicated that fragmentation of the immunoglobulins was the result of *Porphyromonas levii* enzyme activity.

EXAMPLE 4

Production and Assessment of β-Lactamase Enzyme Toxin

The major mechanism of resistance to penicillin and other β-lactam antibiotics is the presence of a group of bacterial enzymes termed β-lactamases. Since their first discovery in the 1940's [33], the widespread use of penicillins is thought to have led to an increased occurrence of β-lactamases [34]. β-lactamases are enzymes capable of hydrolyzing β-lactam antibiotics such as the penicillins and the cephalosporins. They can be chromosomally mediated or plasmid mediated and constitutive or inducible [35]. β-lactamase inhibitors, such as clavulanic acid or sulbactam, can be used to prevent the β-lactamase from inactivating the β-lactam antibiotic, but these inhibitors have slightly different inhibition profiles [36], so the choice of which inhibitor to use will depend on the specific type of β-lactamase present. Specific immunity raised against the enzyme may allow more successful therapy.

Antibiotic Susceptibility Tests: Four anaerobic bacterial isolates of *Prevotella intermedia* were retrieved from storage in Amies medium at −85° C. and plated onto Brucella blood agar (BBA) plates. Penicillin resistance was tested using a disc diffusion method. Colonies from BBA plates were suspended in vials of sterile saline (0.85% NaCl) to reach a turbidity roughly equal to tube 3 of the McFarland turbidity standards (approximate equivalent density of $9.0 \times 10^6$ bacteria/mL). One (1) mL of that suspension was transferred to a fresh BBA plate and spread equally around the plate to create a lawn of bacteria. The plate was allowed to dry before applying two antibiotic discs to the surface of the agar; one disc contained 2 units of penicillin G (P2) and the other contained 10 units (P10). The plate was incubated overnight in an anaerobic chamber at 37° C. and the diameters of any zones of inhibition were measured.

β-Lactamase Testing: Any of the above bacterial isolates showing resistance to penicillin G were tested for β-lactamase activity using commercially available nitrocefin impregnated filter paper discs (Cefinase-BBL). Some results using assay are demonstrated in FIG. 2. Colonies from the antibiotic susceptibility plates and from normal BBA plates were tested to determine if the β-lactamase activity was induced by antibiotic exposure. Colonies removed from an agar plate were smeared onto the disc surface and the disc was observed for a color change for up to 1 h. If the disc changed from yellow to red in color, it was considered to be a positive result, while no color change indicated a negative result. Note that for testing broths or other liquids, a drop of the fluid to be tested was added to the dry disc and then observed for a color change.

Enzyme Isolation: The *Prevotella intermedia* isolates exhibiting β-lactamase activity were used to isolate the β-lactamase itself. As previously outlined, the bacteria of interest were grown in Brain Heart Infusion broth cultures supplemented with 0.005% hemin and 0.5% yeast extract. Three hundred fifty (350) mL broth cultures were made anaerobic by bubbling nitrogen gas through them before autoclaving with tightly sealed caps. The cultures were inoculated, then left to incubate at 37° C. in an anaerobic chamber for 48 h. Following incubation, the broth contents were tested for β-lactamase activity, and a BBA plate was made to check the purity of the culture. The cultures were centrifuged at 5,000×g for 15 min at 4° C. The supernatant was discarded and the pellets resuspended in 50 mM phosphate buffer, pH 7 and centrifuged at 15,000×g for 40 min at 4° C. This washing procedure was repeated once more and the resulting pellet (resuspended in 50 mM phosphate buffer) was sonicated at 60% maximum with 6–7 bursts of 30 seconds each, to disrupt the cells. The sonicate was centrifuged at 27,000×g for 1 h at 4° C. and the supernatant retained for ammonium sulfate precipitation. β-lactamase activity was periodically re-checked throughout the enzyme preparation.

Ammonium Sulfate Precipitation: The supernatant from the above procedure was subjected to ammonium sulfate precipitation [37] to begin the purification process. Sufficient ammonium sulfate was initially added to achieve 40% saturation and the mixture was stirred on ice for 20 min. This was then centrifuged at 10,000×g for 20 min at 4° C. The pellet was resuspended in 50 mM phosphate buffer and saved as the 40% saturation fraction, while the supernatant was used further in the precipitation. Taking into account how much ammonium sulfate had already been added, enough ammonium sulfate was added to bring the supernatant to 50% saturation. This was stirred over ice for 20 min then centrifuged at 10,000×g for 20 min at 4° C. The pellet was resuspended and saved as the 40–50% saturation fraction. The procedure was repeated once more for 60% saturation, after which the resuspended pellet was saved at the 50–60% fraction and the supernatant was saved as the greater than 60% fraction. The ammonium sulfate was removed from the four fractions by overnight dialysis using dialysis tubing with a molecular weight cut-off of 25,000

Daltons in a flask with distilled water constantly flowing through. The samples were then tested for β-lactamase activity and those fractions testing positive were used as enzyme isolates.

Gel Electrophoresis: The isolated enzyme fraction was run on a 7% SDS PAGE, and then stained with silver stain to visualize proteins in the sample.

Antibiotic susceptibility tests were performed on the bacterial isolates. Results are shown in Table 1. *Prevotella intermedia* isolates 5-2, 8-2 and 14-7 showed zones of what has been called regrowth. There was indeed a zone of inhibition, but within that zone of inhibition, there was re-growth immediately around the antibiotic disc. *Bacteroides fragilis* (7-6) was clearly resistant to penicillin.

TABLE 1

Zones of Inhibition of Isolates from Bovine Footrot Tissue Samples

| Isolate Identification | P2 zone of inhibition (mm) | P10 zone of inhibition (mm) |
| --- | --- | --- |
| Prevotella intermedia (5-2) | 22 (with regrowth) | 28 (with regrowth) |
| Bacteroides fragilis (7-6) | 0 | 0 |
| Prevotella intermedia (8-2) | 27 (with regrowth) | 35 (with regrowth) |
| Prevotella intermedia (14-7) | 34 (with 22 mm regrowth) | 38 (with 23 mm regrowth) |

β-Lactamase Testing results are shown in Table 2, and demonstrate that *Prevotella intermedia* isolates 5-2, 8-2 and 14-7 produced β-lactamase.

TABLE 2

β-lactamase Test Results from Footrot Isolates Grown on Two Media Types

| Isolate Identification | Antibiotic Susceptibility Plate | BBA Plate |
| --- | --- | --- |
| Prevotella intermedia (5-2) | positive | positive |
| Bacteroides fragilis (7-6) | strongly positive | strongly positive |
| Prevotella intermedia (8-2) | positive | positive |
| Prevotella intermedia (14-7) | positive | positive |

Isolates of *Porphyromonas levii* were found to be sensitive to the antibiotic penicillin G and were β-lactamase negative.

Enzyme activity of the ammonium sulfate precipitation fractions from strain 7-6 (*B. fragilis*) was found in the 50–60% fraction, but with 5-2 (*P. intermedia*) the enzyme was found in the 40–50% fraction.

Results of gel electrophoresis are illustrated in FIG. 3. These fractions contained enzyme activity, although the activity has not yet been attributed to any single protein band within the fractions.

EXAMPLE 5

Experimental Infection Model

Experimental Animals: Yearling Canadian Simmental crossbred steers (400 kg) were used for this investigation (n=6). Each animal was individually identified with an eartag and commingled in a large pen. Steers were fed a diet of good quality hay ad libitum and fresh water. Animals were obtained from a single source and held for seven days prior to the initiation of the study. Animals were examined by a veterinarian to ensure suitability for the study. All procedures were conducted according to the guidelines of the Canadian Council on Animal Care.

Growth of Bacteria: *Porphyromonas levii* and *Prevotella intermedia*, both of which were isolated from the subcutaneous tissues of feedlot animals affected with acute footrot, were grown separately on kanamycin:vancomycin laked blood agar for five days under conditions of $5\%H_2:5\%CO_2:90\%N_2$ at 37° C. A single colony of each organism was inoculated into modified chopped meat medium (BBL) and grown for 24 h at 37° C. in an anaerobic chamber. *Fusobacterium necrophorum* (ATCC 27852) was grown anaerobically for five days on chocolate agar, and a single colony was inoculated into modified chopped meat medium and grown under anaerobic conditions for 24 h, as described above. Samples of washed cells from broth culture were serially diluted and spread on agar to determine the precise number of viable bacteria (CFU/ml) in each suspension of bacteria. All manipulations were conducted under anaerobic conditions and these bacteria were not exposed to air until immediately prior to injection into the interdigital region of the steers.

Experimental Infection: The animals were individually restrained in a head gate and squeeze apparatus and the left hind foot lifted and restrained with rope. The interdigital region of the foot was carefully cleaned with water and a disinfectant solution and rinsed with 70% ethanol:water (vol:vol). Local anaesthesia was employed using lidocaine and the interdigital skin was excoriated using mechanical abrasion. *Porphyromonas levii* and *Fusobacterium necrophorum*, or *Prevotella intermedia* and *Fusobacterium necrophorum*, were drawn into a common syringe. This mixture (1.0 ml), containing $10^9$ of each of the two organisms, was injected into the interdigital skin and subcutaneous tissue (0.5 ml per location). Three steers received *Porphyromonas levii* mixed with *Fusobacterium necrophorum* (Group 1) and three steers received *Prevotella intermedia* mixed with *Fusobacterium necrophorum* (Group 2). The animals were monitored closely after experimental inoculation for any immediate adverse reactions and daily thereafter.

Clinical Scoring: The severity of clinical signs present in each animal following experimental infection was monitored and scored using a slight modification of a previously published scoring system [17]. Briefly, this involved daily examination of the animal and subjective assessment of the lameness, lesion, and swelling.

Lameness was evaluated daily as:

0=normal

1=slight lameness—puts some weight on foot but moves readily

2=moderate lameness—does not want to put weight on foot and moves slowly

3=severe lameness—holds foot up at intervals and is reluctant to move or place weight on the foot (prefers to lie down)

Swelling was evaluated and scored daily as:

0=no swelling

1=slight to moderate swelling

2=moderate to severe swelling

3=severe swelling

Lesions were evaluated and scored daily as:
0=no lesions
1=lesion healed or healing
2=small interdigital lesion extending up to ¼ to ½ length of the interdigital space
3=very large necrotic lesion involving almost all of the interdigital space Scores for lameness, swelling, and lesions were totaled to arrive at a footrot score.

Biopsy Sampling of Subcutaneous Tissue: Tissue biopsy specimens were obtained from each experimentally infected animal six days after inoculation with bacteria, and immediately prior to antibiotic therapy. Each animal had its affected foot physically restrained using ropes. The foot was lifted and cleaned using water and disinfectant solution followed by 70:30 (vol/vol) ethanol:water. Local anaesthesia was applied and a small incision was made using a scalpel blade (#10) over a swollen portion of the limb immediately proximal to the affected region of the foot. A Trucut™ hepatic biopsy needle was inserted into the subcutaneous tissue. A core of tissue was collected and transported immediately to the laboratory in anaerobic transport medium. A second biopsy specimen was collected from each animal and fixed in 10% neutral buffered formalin for histology.

Bacteriology: Tissue samples were placed in modified chopped meat medium and incubated at 37° C. under anaerobic conditions. Periodically, a small sample of broth was removed from the broth culture and streaked on kanamycin:vancomycin laked blood agar, Brucella agar, and on chocolate agar to obtain single colonies of the anaerobic bacteria present. Isolates were presumptively identified based on colony morphology and pigmentation, fluorescence under longwave UV light, gram stain reaction, cellular morphology, antibiotic resistance (kanamycin, vancomycin, colistin), catalase production, nitrate test, indole test, lipase production on egg yolk agar, and the urease and oxidase tests.

Antibiotic Sensitivity of Bacterial Isolates: Bacteria were grown anaerobically on kanamycin:vancomycin laked blood agar for colony isolation and purity. Isolates were then inoculated into 10 ml of modified chopped meat medium and incubated anaerobically at 37° C. in an environmental chamber. Oxytetracycline hydrochloride and a macrolide antibiotic were diluted in medium to a concentration of 640 μg/ml. Serial dilutions (1.1) were made for both compounds to yield stock solution ranging from 640 ug/ml to 0.0625 ug/ml. Falcon 3072 Micro Test III™ tissue culture plates with lids were loaded in triplicate with 100 μl of each concentrations (MIC). Each drug concentration was inoculated with 100 μl of bacterial broth inoculum. The inoculum diluted 1:1 in sterile PBS (pH 7.2) served as a control. Drug stock solution was also aliquoted to measure absorbance capabilities (650 nm). Plates were incubated for 24 h anaerobically at 37° C. The broth inoculum was serially diluted, plated on kanamycin:vancomycin laked blood agar and incubated anaerobically for viable counts (CFU/ml). After the incubation period, 20 ul of inoculum-drug combination was removed from one series of each descending drug concentration and plated on kanamycin:vancomycin laked blood agar to determine minimum bactericidal concentration (MBC) values. All MBC plates were incubated for seven days under anaerobic conditions. The tissue culture plates were then read on a microplate reader using SOFTmax Version 2.32 software. Mean absorbance (650 nm) readings and grey scale analysis were used to determine the MIC for each drug and isolate tested. The MBC was determined by the drug concentration which exhibited a 99.9% reduction of CFU/ml count.

All six steers were normal and healthy prior to the study. No concurrent disease occurred during the period of this study. All six steers developed a clinical condition consistent with acute footrot within five days following inoculation of the bacteria into the subcutaneous tissue and the skin of the interdigital cleft. Each of the six animals was also clinically lame by five days post-inoculation with bacteria.

Biopsy specimens were successfully obtained from all animals on the sixth day following experimental infection. In each case anaerobic bacteriology produced the re-isolation of the organisms initially injected into the feet. Microscopic lesions were very similar in all steers. Typical lesions involved coagulative necrosis and edema of the subcutaneous tissues and an infiltration of local tissue with monocytic inflammatory cells. Very few neutrophils were seen; however, biopsy samples were taken six days after exposure to the bacteria. An incubation period of five days after inoculation with bacteria may suggest that an initial failed neutrophilic response followed by a more chronic monocytic infiltration may precede clinical signs in this model infection. The implications of this finding in natural infections of footrot are not known. Morphotypic bacteria were visible in stained sections of the biopsy specimens.

EXAMPLE 6

Assessment of the Effectiveness of a Macrolide Antibiotic to Treat Footrot

Treatment: Six days following experimental inoculation of feet with bacteria, and immediately following biopsy specimen collection, all steers from Example 5 were treated with a single subcutaneous administration of a macrolide antibiotic at a dosage of 10 mg per kilogram body weight. Response to the therapy was monitored by clinical scoring, as outlined above. Twenty-four (24) hours following administration of the antibiotic, the feet were prepared for biopsy sampling of subcutaneous tissue and a third biopsy taken, held on dry ice for transportation to the laboratory, frozen in $N_{2(1)}$, and stored at −85° C.

Histology: Tissue specimens fixed in 10% neutral buffered formalin were dehydrated in solutions of increasing ethanol concentration followed by three 15 min exposures to absolute ethanol. The specimens were then infiltrated with and embedded in meta-methacrylate. Sections (1.5 μm) were cut on a microtome, heat fixed on microscope slides, and stained with buffered methylene blue and basic fuchsin [19]. Coverslips were fixed on slides with mounting medium and sections were viewed and photographed on a microscope.

Statistical Analysis: Clinical scores were evaluated by comparison to pre-exposure scores in the same groups of animals using nonparametric analysis of variance and Kruskal Wallis tests. Data of Group 1 and Group 2 were compared by nonparametric analysis of variance and Mann Whitney tests. In all cases the P value was 0.05. The mean total footrot scores for animals in Group 1 and Group 2 are shown in FIG. 6A and FIG. 6B, respectively. In the *Porphyromonas levii* infected animals (Group 1) the mean total footrot score from day 7 was significantly reduced following antibiotic therapy on day 6. Scores remained significantly lower than on day 6 and continued to decrease from day 8 to day 17. In the *Prevotella intermedia* infected animals (Group 2) there was a reduction in clinical score; however, the reduction was not statistically significant. FIG. 7 demonstrates the mean total footrot scores from all six animals (irrespective of group). There was significant improvement in the footrot score in five of the six animals following treatment and this reduction in clinical score was maintained for the entire 17 days of the experiment. The single failure (animal number YEL398) was initially the most severely affected animal following experimental infection. It did not respond to a single administration of the macrolide antibiotic, or to a second administration of the drug 48 h later. Treatment with ceftiofur sodium at a dosage of 1.0 mg ceftiofur per kg body weight q24 h for five days was implemented following the initial treatment course. The steer retained a subtle and permanent lameness and was eventually euthanized 30 days following the last treatment and given a necropsy examination. The post mortem examination revealed fibrosis of the lateral branch of the long digital extensor tendon. There was no evidence of active infection grossly or histologically. FIG. 8 shows the mean total footrot scores of animals excluding the non-responding YEL398.

Table 3 demonstrates the minimum inhibitory concentrations and minimum bactericidal concentrations of the three strains of bacteria used to experimentally infect feet. The MIC of the organisms re-isolated from infected feet immediately prior to administration of macrolide antibiotic did not differ substantially from those in Table 3.

TABLE 3

MIC and MBC of Macrolide Antibiotic

| Bacteria | MIC (µg/ml) | MBC (µm/ml) |
| --- | --- | --- |
| Porphyromonas levii | <0.03 | >32 |
| Prevotella intermedia | 4 | 32 |
| Fusobacterium necrophorum | 0.13 | 4 |

The macrolide antibiotic tested in the experimental model was effective in treating five of six animals (83.3%) with experimentally-induced acute footrot. This occurred despite seemingly unfavorable MBC value for both *Porphyromonas levii* and *Prevotella intermedia*. This antibiotic is concentrated within monocytic cells, such as macrophages, at levels much higher than those found in serum and tissue. The ability of these tissue macrophages to kill bacteria may be accentuated in the presence of intracellular antibiotic and this may be a fundamental reason for the success of the antibiotic with bacteria having unfavorable MBC's. Although more data are required to fully establish the usefulness of this antibiotic in bovine footrot, it may be an effective antibiotic for use in this disease based on its performance in the experimental model for this disease.

EXAMPLE 7

Immunization of Cattle Study

General Design and Blood Sampling Times: A total of 26 individually identified cattle were used for this study. They were randomly allocated to one of the following groups: 1] immunized or 2] sham-immunized. Prior to immunization each animal had a venous blood specimen collected from the jugular vein by standard venipuncture technique (day 0). Serum was separated from this blood specimen and stored frozen at −85° C. Animals were immunized on day 1. Blood samples for serum were collected three weeks following initial immunization (day 21) when the animals received a second immunization (booster injection of identical preparation). Seven days following the booster injections (day 28) sera were collected again, and the cattle were inoculated with viable *Porphyromonas levii* and *Fusobacterium necrophorum*, as described in Example 5. Serum samples were collected again on day 35, day 42 and at six months.

Vaccination: Cattle were immunized with: 1] an inactivated whole cell vaccine composition (bacterin) composed of a snap-frozen:thawed preparation of *Prevotella intermedia* and *Porphyromonas levii*, as described above, and alum adjuvant or 2] saline and alum adjuvant. The bacterin contained approximately 0.5 to 0.75 mg protein per ml and each animal received about 1 ml of bacterin containing about 0.75 mg of protein prepared with commercially available alum-based adjuvant by a subcutaneous route. Animals were immunized or sham-immunized on day 1 and day 21. The bacterins were assessed for IgG protease activity by the methods outlined in Example 3 and for β-lactamase activity using nitrocefin discs, as described in Example 4. The *P. levii* bacterin was found to have protease activity but no β-lactamase activity, while the *P. intermedia* bacterin was found to have β-lactamase activity but no protease activity.

Clinical Response: The individual animals were the experimental unit. Clinical scores were assigned daily to animals, using the system described in Example 5, by an individual blinded to experimental group. Cattle that were vaccinated had lower clinical scores than sham vaccinated controls during experimentally induced infection.

This study demonstrated that pre-exposure immunization with *Porphyromonas levii* and *Prevotella intermedia* resulted in the production of serum antibody that were protective in experimental footrot infections. The serum antibody specifically reacting to *Porphyromonas levii* and *Prevotella intermedia* was more abundant in immunized animals than in sham-immunized animals. In particular, levels of serum IgG specific for *P. levii* were significantly higher than the levels in sham vaccinated animals both during and following experimental infection, i.e., between day 28 and 187. The serum antibodies reactive to *Fusobacterium necrophorum* were similar in groups of immunized animals and sham-immunized animals during the entire duration of the experiment (all time points sampled). The antibodies produced by animals immunized with our vaccine conveyed protection from severity of experimental infection compared to sham-immunized animals, as measured by clinical response and scoring. The severity of experimental infection within individual animals generally correlated with the serum antibody response in those individual animals.

EXAMPLE 8

Neutrophil-Mediated Phagocytosis and the Production of Immunoglobulin $G_2$ Protease by *Porphyromonas Levii*

Methods: PMN were purified from whole bovine blood, quantified, assessed for viability, and exposed to one of three putative etiologic agents of AIP (*Porphyromonas levii, Prevotella intermedia, Fusobacterium necrophorum* ATCC 27852) or latex beads and assessed for phagocytosis using direct microscopy. The effects of bovine serum specifically raised against *P. levii* on antibody-mediated phagocytosis by PMN (opsonization) were examined. *P. levii* was examined for the presence of protease activity capable of cleaving bovine Ig (IgG, IgM, $IgG_1$, $IgG_2$).

Blood Collection and PMN Purification: Whole bovine blood was collected in acid citrate dextrose by jugular venipuncture. The erythrocyte fraction was separated by centrifugation and this fraction subjected to repeated cold hypotonic lysis [38]. PMN purified in this fashion were pelleted by centrifugation, resuspended in sterile pyrogen-free PBS, enumerated by haemacytometry, viability determined by staining with 0.1% trypan blue, and assessed for differential leukocyte population on cytospin preparations. Preparations were required to be a minimum 95% pure and 95% viable for assays to be performed.

Antibody Production and Evaluation: A calf with low pre-exposure titres to all three bacterial antigen preparations was used. *P. levii* was grown in anaerobic conditions, killed with 10% buffered formalin, washed three times, suspended at 1.0 mg protein per mL, and mixed with alum adjuvant prior to immunization of the calf. The calf received a booster injection 21 days later with the appropriate antigen preparation. Antibody titres were determined by ELISA using killed whole cells of *P. levii* as the antigen preparation.

Phagocytosis Assays: Purified viable PMN ($1.0 \times 10^6$ cells/mL) were incubated for 15 min (37° C.) with $1.5 \times 10^7$ bacteria/mL following pre-exposure of bacteria to either sterile pyrogen-free PBS, low titre serum, or high titre serum for 30 min. The mixture was centrifuged to pellet PMN, the cells re-suspended in PBS, and the solution cytospinned and stained with Diff-Quik stain for microscopic viewing. Counts of PMN cells phagocytosing bacteria per total cells were determined and photographs were taken.

Protease Preparation, Ig Biotinylation, and Ig Protease Assay: Supernatant of a broth culture of *P. levii* grown in anaerobic conditions (5% $H_2$: 5% $CO_2$: 90%$N_2$) in supplemented cooked meat broth (haemin, Vitamin K) at 37° C. for four days was collected by centrifugation and stored (−80° C.) until used in the protease assay. Culture purity was assured by streak plating onto BBA and standard bacteriological identification.

N-hydroxy-succinomidobiotin was dissolved in dimethyl sulfoxide and was added to each of bovine IgG, IgM, $IgG_1$ and $IgG_2$ (1:10 wt/vol), the Igs were incubated for 2 h (25° C.), and the reaction terminated with 1 mg of glycine. The biotinylated Igs were dialyzed 14 h in three changes of double distilled water and final protein concentrations were determined by Bradford assay [39].

The protease assay was a slight modification of the methods of Lee and Shewen [24]. Biotinylated IgG (10 μg) was added to 250 μL of supernatant and 2.5 μL of penicillin-streptomycin solution (penicillin G 100 U/mL, streptomycin 100 μg/mL). The protease assay was carried out at 30, 35 and 40° C. and optimal assay temperature was determined to be 35° C. Samples (10 μL) were taken at 0, 0.5, 1, 2, 4, 8, 24, 48, and 72 h and added to 10 μL of SDS PAGE sample buffer [30], boiled for 4 min, followed by electrophoretic separation by SDS PAGE. Control assays included *P. levii* supernatant heated to 100° C. prior to exposure to the biotinylated Igs as well as uninoculated cooked meat medium and distilled water.

All samples were resolved in 15% SDS PAGE gels using a 4% stacking gel and standard methodology. Gels were run on ice at 150V for 15 min followed by 200V for 45 min in 10% running buffer. Protein in the gels was transferred to nitrocellulose [31] at 20V for 14 h at 4° C., washed in blocking solution (1 h at 37° C.), washed with TBS-tween buffer (3×15 min 20° C.), and incubated with streptavidin-alkaline phosphatase (1:5000) in TBS-tween for 2 h at 37° C. Blots were again washed three times for 15 min in TBS-tween and nitroblue tetrazolium (NBT) and 5-bromo-4 chloro-3 indolyl phosphate (BCIP) were added as substrate for color development (4 min) in buffer (31.52 g Tris-HCL, 0.18 g $MgCl_2$-$6H_2O$, 1 l distilled water, pH 8.8). BCIP was initially dissolved in DMSO. Protein bands representing the light and heavy chains of the biotinylated immunoglobulins, or fragments of these immunoglobulin chains, were viewed based on alkaline phosphatase activity on the nitrocellulose. Photographs were obtained immediately.

Results of Phagocytosis Assays: Comparisons of the ability of bovine PMN to phagocytose each of the putative etiologic agents of AIP are shown in Table 4. Values are expressed as mean cells phagocytosing bacteria per 100 PMN±SD (n value is 9 per data point). *=significantly different than all other experimental groups (P<0.05). Bovine PMN readily phagocytose *P. intermedia* and *F. necrophorum*, but the ability of the cells to phagocytose *P. levii* was significantly reduced compared to these groups and to PBS controls (P<0.05).

TABLE 4

Comparison of Phagocytosis by Bovine PMN in vitro of Latex Beads, *P. levii*, *P. intermedia* and *F. necrophorum*

| Experimental Group | Phagocytosis |
|---|---|
| Latex beads | 17.9 ± 3.8 |
| *P. levii* | 5.3 ± 1.6* |
| *P. intermedia* (8-2) | 60.7 ± 6.1 |
| *F. necrophorum* | 64.1 ± 4.4 |

The phagocytic abilities of PMN for *P. levii* when the bacteria were pre-incubated with PBS, low titre anti-*P. levii* serum, high titre anti-*P. levii* serum, or complement-destroyed high titre anti-*P. levii* serum were examined. High levels of phagocytosis were evident in these same cell preparations if the *P. levii* were pre-incubated with high titre anti-*P. levii* bovine serum. This restoration of phagocytic function was not altered substantially by heating the serum at 56° C. for 30 min (Table 5). *=significantly greater than both PBS control and low titre serum (P<0.05) but not different from complement destroyed serum.

TABLE 5

Examination of Phagocytosis Abilities of PMN for *P. levii* when Incubated with Anti-*P. levii* Serum

| Experimental Group | Phagocytosis |
|---|---|
| *P. levii* and PBS | 5.3 ± 1.6 |
| *P. levii* and low Ig | 30.0 ± 5.5 |
| *P. levii* and high Ig | 97.0 ± 1.1* |
| *P. levii* and inact. complement factors | 89.9 ± 3.8* |

Ig Protease Assays: Nitrocellulose transfer of biotinylated IgG exposed to culture supernatant of *P. levii* is shown in FIG. 9A. From left to right are increasing times (hours) of exposure. Lane A=0, Lane B=0.5, Lane C=1, Lane D=2, Lane E=4, Lane F=8, Lane G=24, Lane H=48, and Lane I=72 h time samples. Results show the presence and increasing intensity of the degradation bands (major bands are highlighted with arrows) smaller than the heavy and light chains (arrowheads) as incubation time increases. Also, near complete degradation of the heavy chain by 24 h was noted.

In contrast, nitrocellulose transfer of biotinylated IgM exposed to culture supernatant of *P. levii* is shown in FIG. 9B. From left to right are increasing times (hours) of exposure. Lane A=0, Lane B=0.5, Lane C=1, Lane D=2, Lane E=8, Lane F=24, Lane G=48, and Lane H=72 h time samples. There is absence of degradation bands. Only the light and heavy chains (arrowheads) of IgM are evident.

When $IgG_1$ was assayed, degradation bands were not evident (FIG. 10A) and again only bands representing the heavy and light Ig chains could be seen. However, when assays using $IgG_2$ were conducted similar results to those employing crude IgG were seen with degradation bands appearing within 30 min, as illustrated in FIG. 10B, but heavy chain was not as extensively degraded. Controls using water alone, heated supernatant, supernatant extracts of *P. intermedia* or *F. necrophorum,* or uninoculated media (each of which was exposed to the biotinylated IgG) showed no evidence of degradation bands (data not shown).

Modification of the above-described modes of carrying out the various embodiments of this invention will be apparent to those skilled in the art following the teachings of this invention as set forth herein. The examples described above are not limiting, but are merely exemplary of this invention, the scope of which is defined by the claims which follow.

REFERENCES

The following references are cited in this application as numbers in brackets [ ] at the relevant portions of the application.

1. Egerton, J. R., "Footrot of Cattle, Goats, and Deer" in *Footrot and Foot Abscess of Ruminants,* Egerton, J. R., et al. eds., CRC Press., pp 47–56 (1989).
2. Radostits, O. M., et al., "Bovine Interdigital Necrobacillosis (Foul in the Foot, Footrot)" in *Veterinary Medicine: A Textbook of the Diseases of Cattle, Sheep, Pigs, Goats and Horses,* 8th Ed., Bailliere Tindal, pp 867–870 (1994).
3. Bergsten, C., "Infectious Diseases of the Digits", in *Lameness in Cattle,* 3rd Ed., Greenough, P. R. ed., W.B. Saunders Co., pp 89–100 (1997).
4. Berg, J. N., "Bacterial Etiology of Diseases in the Footrot Complex: Recent Research and Nomenclature Changes", in *Proceedings and Abstracts of the Eighth International Symposium on Disorders of the Ruminant Digit and International Conference on Bovine Lameness,* Banff, Alberta, Canada, Univ. Saskatchewan Printing Services, p 51 (1994).
5. Volar® *Fusobacterium necrophorum* Bacterin, Bayer, *Veterinary Pharmaceuticals and Biologicals,* 10th Ed., pp 1024–1025 (1997).
6. McGuire, T. C., et al., "Functional Properties of Bovine IgG$_1$ and IgG$_2$: Interaction with Complement, Macrophages, Neutrophils and Skin", *Immun,* 38:249–256 (1979).
7. Taylor, C. E., "Cytokines as Adjuvants for Vaccines: Antigen-Specific Responses Differ from Polyclonal Responses", *Infect Immun,* 63:3241–3244 (1995).
8. Nagaraja, et al., *Fusobacterium necrophorum* Leukotoxoid Vaccine, U.S. Pat. No. 5,455,034 (1995).
9. Nagaraja, et al., Fusobacterium Leukotoxoid Vaccine, U.S. Pat. No. 5,492,694 (1996).
10. Adam, U.S. Pat. No. 4,061,751 (1977).
11. Blood, D.C., et al., Veterinary Medicine: A Textbook of the Diseases of Cattle, Sheep, Pigs, Goats and Horses, 6th Ed., London: Bailliere Tindall, pp 662–665 (1983).
12. Berg, J. N., et al., "*Fusobacterium necrophorum* and *Bacteroides melaninogenicus* as Etiologic Agents of Footrot in Cattle", *Am J Vet Res,* 36(8):1115–1122 (1975).
13. Gupta, R. B., et al., "A study of the Etiology of Footrot in Cattle", *Cornell Vet,* 54:66–77 (1964).
14. Gillespie, J. H., et al., *Hagen and Bruner's Infections Diseases of Domestic Animals,* 7th Ed., Ithaca: Cornell University Press, p 158 (1981).
15. Kruse, G. O. W., et al., "Therapeutic Use of Terramycin Against Footrot in Cattle", in *Proceedings* (Vol II), 15th World Buiatrics Congres, pp 1111–1116 (1988).
16. Morck, D. W., et al., "Comparison of ceftiofur sodium and oxytetracycline for treatment of acute interdigital phlegmon (foot rot) in feedlot cattle", *J Am Vet Med Assoc,* 212(2):254–257 (1998).
17. Morck, D. W., et al., "Experimental Evaluation of a Commercial Footrot Vaccine Against Native Canadian Strains of Dichelobacter Nodosus", *Can J Vet Res,* 58:122–126 (1994).
18. Engelkrik, P. G., et al., "Principles and Practice of Clinical Anaerobic Bacteriology", Belmont: Star Publishing Co., pp 147–180 (1992).
19. Bennet, H. S., et al., "Science and Art of Preparing Tissues Embedded in Plastic for Light Microscopy, with Special Reference to Glycol Methacrylate, Glass Knives and Simple Stains", *Stain Technol,* 51:71–97 (1976).
20. Loomes, et al., "The Cleavage of Immunoglobulin G in vitro and in vivo by a Proteinase Secreted by the Urinary Tract Pathogen Proteus mirabilis", *J Med Micro,* 39:225–232 (1993).
21. Wassif, et al., "Molecular Analysis of a Metalloprotease from Proteus mirabilis", J Bact., 177:5790–5798 (1995).
22. Prokesova, et al., "Cleavage of Human Immunoglobulins by a Serine Protease from *Staphylococcus aureus"*, *Immun Let,* 31:259–256 (1992).
23. Simpson, et al., "Purification, Characterization and Comparison of the Immunoglobulin A1 Proteases of *Neisseria gonorrhoeae"*, J Bact, 170:1866–1873 (1988).
24. Lee, C. W., et al., "Evidence of Bovine Immunoglobulin G$_1$ (IgG$_1$) Protease Activity in Partially Purified Culture Supernate of *Pasteurella haemolytica* A1", *Can J Vet Res,* 60:127–132 (1996).
25. Kuby, *J Immun,* 2nd Ed., New York: W. H. Freeman and Company, pp 124–127 (1994).
26. Sawyer, D. W., et al., "Polymorphonuclear Neutrophils: An Effective Antimicrobial Force", *Rev Infect Dis,* 11:S1532–S1544 (1989).
27. Mossman, et al., "Antibody-Dependent Cell-Mediated Cytotoxicity in Cattle: Transfer of IgG Subclasses in Relation to the Protection of the Newborn Calf", in Butler, et al., eds., *The Ruminant Immune System,* New York: Plenum Press, pp 279–291(1981).
28. Kacsovics, I., et al., "The Heterogeneity of Bovine IgG$_2$-VIII. The Complete cDNA Sequence of Bovine IgG$_2$ (A2) and an IgG$_1$", *Mol Immun,* 33:189–195 (1996).
29. Heyermann, H., et al., "The Heterogeneity of Bovine IgG$_2$-V. Differences in the Primary Structure of Bovine IgG$_2$ Allotypes", *Mol Immun,* 29:1147–1152 (1992).
30. *Remington's Pharmaceutical Sciences,* 18th Ed., Mack Publishing Company (1990).
31. Laemmli, U. K., "Cleavage of Structural Protein During the Assembly of the Head Bacteriophage T4", *Nature,* 227:680–685 (1970).
32. Towbin, H., "Electrophoretic Transfer of Proteins from Polyacrylamide Gels to Nitrocellulose Sheets: Procedure and Some Applications", *Proc Natl Acad Sci,* 76:4350–4354 (1979).
33. Abraham, E. P., et al., "An Enzyme from Bacteria Able to Destroy Penicillin" [letter], Nature, 146:837 (1940).
34. Rolinson, G. N., "Evolution of β-Lactamase Inhibitors", *Rev of Infect Dis,* 13(Suppl 9):S727–732 (1991).
35. Moellering, Robert C., Jr., "β-Lactamase Inhibition: Therapeutic Implications in Infectious Diseases—An Overview", *Rev of Infect Dis,* 13(Suppl 9):S723–726 (1991).
36. Bush, Karen, "β-Lactamase Inhibitors from Laboratory to Clinic", *Clin Microbio Rev,* 1(1):109–123 (1988).
37. Schleif, Robert F., et al., *Practical Methods in Molecular Biology,* Springer-Verlag, New York, Inc., pp 62–64 (1981).
38. Chin, A., et al., "Anti-Inflammatory Benefits of Tilmicosin in the *Pasteurella haemolytica*-Infected Lung", (in press) (1998).

39. Bradford, M. M., "A Rapid and Sensitive Method for the Quantitation of Microgram Quantities of Protein Utilizing the Principle of Protein-Dye Binding", *Annal Biochem*, 72:248–254 (1976).

The disclosure of the above publications and patents are herein incorporated by reference in their entirety to the same extent as if the language of each individual publication or patent were specifically and individually included herein.

We claim:

1. A method of preventing or treating footrot in an animal suffering from or susceptible to footrot comprising administering to said animal an effective amount of a composition comprising:

a) at least one immunogen selected from the group consisting of Prevotella associated with bovine footrot, Porphyromonas associated with bovine footrot, a subunit of Prevotella or Porphyromonas and a toxin of Prevotella or Porphyromonas; and b) a pharmaceutically acceptable carrier.

2. The method of claim 1 wherein said composition is administered parenterally or orally.

3. The method of claim 1 wherein said administration is parenteral administration selected from the group consisting of subcutaneous, intramuscular, intraperitoneal, intranasal, local (intrapodal), and intravenous administration.

4. The method of claim 1 wherein said administration is performed two or more times.

5. The method of claim 4 wherein said administration comprises annual administration.

6. The method of claim 1, which prevents symptoms of footrot.

7. The method of claim 1, which inhibits the function of at least one agent selected from the group consisting of proteases of bacteria associated with footrot, an $IgG_2$ protease of *Porphyromonas levii* and a β-lactamase of *Prevotella intermedia*.

* * * * *